(12) United States Patent
Mirelman et al.

(10) Patent No.: US 10,945,641 B2
(45) Date of Patent: Mar. 16, 2021

(54) VIRTUAL REALITY FOR MOVEMENT DISORDER DIAGNOSIS AND/OR TREATMENT

(71) Applicant: The Medical Research, Infrastructure and Health Services Fund of the Tel Aviv Medical Center, Tel-Aviv (IL)

(72) Inventors: Anat Mirelman, Ramat-Gan (IL); Jeffrey M. Hausdorff, Hashmonaim (IL); Nir Giladi, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 350 days.

(21) Appl. No.: 14/350,567

(22) PCT Filed: Oct. 9, 2012

(86) PCT No.: PCT/IB2012/055453
§ 371 (c)(1),
(2) Date: Apr. 9, 2014

(87) PCT Pub. No.: WO2013/054257
PCT Pub. Date: Apr. 18, 2013

(65) Prior Publication Data
US 2014/0276130 A1    Sep. 18, 2014

Related U.S. Application Data

(60) Provisional application No. 61/545,161, filed on Oct. 9, 2011, provisional application No. 61/545,164, filed on Oct. 9, 2011.

(51) Int. Cl.
*A61B 5/11*    (2006.01)
*A61B 5/00*    (2006.01)
(Continued)

(52) U.S. Cl.
CPC .......... *A61B 5/1104* (2013.01); *A61B 5/0476* (2013.01); *A61B 5/112* (2013.01);
(Continued)

(58) Field of Classification Search
CPC .... A61B 2505/09; A61B 5/1117; A61B 5/112
See application file for complete search history.

(56) References Cited

U.S. PATENT DOCUMENTS

| 6,050,822 A | 4/2000 | Faughn |
| 8,409,116 B2 | 4/2013 | Wang et al. |

(Continued)

FOREIGN PATENT DOCUMENTS

| WO | WO 2010/150260 | 12/2010 |
| WO | WO 2013/054257 | 4/2013 |
| WO | WO 2013/054258 | 4/2013 |

OTHER PUBLICATIONS

Mansfield et al, A perturbation-based balance training program for older adults: study protocol for a randomised controlled trial, 2007, BMC Geriatrics, 7(12): 1-14.*

(Continued)

*Primary Examiner* — Jacqueline Cheng
*Assistant Examiner* — Jairo H Portillo

(57) ABSTRACT

Methods and/or systems for diagnosing, monitoring and/or treating persons at risk for falling and/or other pathological conditions. In an exemplary embodiment of the invention, people are diagnosed before they actually start falling. Optionally, the diagnosis includes trying out and identifying one or more fall triggers using virtual reality tools. Optionally or alternatively, treatment includes training the persons using situations and/or triggers which are determined to be relevant for that person.

52 Claims, 19 Drawing Sheets

Effects of TT+VR on Fall risk Mediators

(51) Int. Cl.

| A61B 5/0476 | (2006.01) |
| A61B 5/16 | (2006.01) |
| G06F 19/00 | (2018.01) |
| A61B 5/0484 | (2006.01) |
| A61B 5/0205 | (2006.01) |
| A61B 5/026 | (2006.01) |

(52) U.S. Cl.
CPC ............ *A61B 5/1117* (2013.01); *A61B 5/162* (2013.01); *A61B 5/744* (2013.01); *G06F 19/00* (2013.01); *A61B 5/0205* (2013.01); *A61B 5/026* (2013.01); *A61B 5/04842* (2013.01); *A61B 5/1118* (2013.01); *A61B 5/7203* (2013.01); *A61B 5/7257* (2013.01); *A61B 2505/09* (2013.01)

(56) References Cited

U.S. PATENT DOCUMENTS

| 8,744,587 | B2 | 6/2014 | Miesel et al. |
| 2003/0077556 | A1* | 4/2003 | French ................ A61B 5/1113 434/258 |
| 2006/0247104 | A1 | 11/2006 | Grabiner et al. |
| 2007/0129622 | A1 | 6/2007 | Bourget et al. |
| 2008/0162088 | A1* | 7/2008 | DeVaul ................ A61B 5/0024 702/190 |
| 2008/0252445 | A1* | 10/2008 | Kolen ................ G08B 21/0446 340/539.16 |
| 2009/0124938 | A1* | 5/2009 | Brunner ................ A61B 5/1038 600/595 |
| 2009/0240170 | A1 | 9/2009 | Rowley et al. |
| 2010/0228144 | A1 | 9/2010 | Labat |
| 2014/0303508 | A1 | 10/2014 | Plotnik-Peleg et al. |
| 2017/0258370 | A1 | 9/2017 | Plotnik-Peleg et al. |

OTHER PUBLICATIONS

McAndrew et al, Walking variability during continuous pseudo-random oscillations of the support surface and visual field, 2010, Journal of Biomechanics, 43(8): 1470-1475.*

Jacobs et al, Changes in the activity of the cerebral cortex relate to postural response modification when warned of a perturbation, 2008, Clin Neurophysiol., 119(6): 1431-1442.*

Iseki et al, Gait disturbance associated with white matter changes: a gait analysis and blood flow study, 2010, Neuroimage, 49(2): 1659-1666.*

Nakamura et al, Postural and gait disturbance correlated with decreased frontal cerebral blood flow in Alzheimer disease, 1997, Alzheimer Dis Assoc Disord, 11(3): 132-139.*

Holden, Virtual Environments for Motor Rehabilitation: Review, 2005, Cyber Psychology & Behavior, 8(3): 187-219.*

Chen et al (Stepping Over Obstacles: Dividing Attention Impairs Performance of Old More Than Young Adults, 1996, J Gerontol A Biol Sci Med Sci, 51(3): M116-22).*

Fung et al (A Treadmill and Motion Coupled Virtual Reality System for Gait Training Post-Stroke, 2006, Cyberpsychol Behav, 9(2):157-62).*

Weerdesteyn et al (Gait adjustments in response to an obstacle are faster than voluntary reactions, 2004, Human Movement Science, 23(3-4): 351-63).*

Rand et al (Virtual reality rehabilitation for all: Vivid GX versus Sony PlayStation II EyeToy, 2004, Proc. 5th Intl Conf. Disability, Virtual Reality & Assoc. Tech., Oxford, UK, 87-94).*

International Search Report and the Written Opinion dated Feb. 28, 2013 From the International Search Authority Re. Application No. PCT/IB2012/055453.

International Search Report and the Written Opinion dated Feb. 28, 2013 From the International Search Authority Re. Application No. PCT/IB2012/055454.

Ags et al. "Guideline for the Prevention of Falls in Older Persons", Journal of the American Geriatrics Society, JAGS, 49(5): 664-672, May 2001.

Bachlin et al. "A Wearable System to Assist Walking of Parkinson's Disease", Methods of Information in Medicine, 49(1): 88-95, 2010.

Bakker et al. "Recent Advances in Functional Neuroimaging of Gait", Journal of Neural Transmission, 114(10): 1323-1331, Oct. 31, 2007.

Brichetto et al. "Evaluation of Physical Therapy in Parkinsonian Patients With Freezing of Gait: A Pilot Study", Clinical Rehabilitation, 20(1): 31-35, Jan. 2006.

Chee et al. "Gait Freezing in Parkinson's Disease and the Stride Length Sequence Effect Interaction", Brain, 132: 2151-2160, 2009.

Delbaere et al. "Development and Validation of Fall Risk Screening Tools for Use in Residential Aged Care Facilities", Medical Journal of Australia, 189(4): 193-196, Aug. 18, 2008.

Fasano et al. "Modulation of Gait Coordination by Subthalamic Stimulation Improves Freezing of Gait", Movement Disorders, 26(5): 844-851, Apr. 2011.

Frazzitta et al. "Rehabilitation Treatment of Gait in Patients With Parkinson's Disease With Freezing: A Comparison Between Two Physical Therapy Protocols Using Visual and Auditory Cues With or Without Treadmill Training", Movement Disorders, 24(8): 1139-1143, 2009.

Frenkel-Toledo et al. "Treadmill Walking as an External Pacemaker to Improve Gait Rhythm and Stability in Parkinson's Disease", Movement Disorders, 20(9): 1109-1114, 2005.

Galica et al. "Subsensory Vibrations to the Feet Reduce Gait Variability in Elderly Fallers", Gait & Posture, 30: 383-387, 2009.

Ganz et al. "Will My Patient Fall?", The Journal of the American Medical Association, 297(1), 77-86, Jan. 3, 2009.

Giladi et al. Freezing Phenomenon in Patients With Parkinsonian Syndromes, Movement Disorders, 12(3): 302-305, 1997.

Giladi et al. "Understanding and Treating Freezing of Gait in Parkinsonism, Proposed Working Definition, and Setting the Stage", Movement Disorders, 23(2): S423-S425, 2008.

Hausdorff et al. "Impaired Regulation of Stride Variability", Experimental Brain Research, 149(2): 187-194, Mar. 2003.

Hausdorff et al. "Rhythmic Auditory Stimulation Modulates Gait Variability in Parkinson's Disease", European Journal of Neuroscience, 26(8): 2369-2375, 2007.

Herman et al. "The Dynamic Gait Index in Healthy Older Adults: The Role of Stair Climbing, Fear of Falling and Gender", Gait & Posture, 29: 237-241, 2009.

Higgins "Advances in Neurology", 67: 314, 1996.

Hong et al. "Rotating Treadmill Training Reduces Freezing in Parkinson Disease: Preliminary Observations", Parkinsonism & Related Disorders, 14(4): 359-363, May 2008.

Iansek et al. "The Sequence Effect and Gait Festination in Parkinson Disease: Contributors to Freezing of Gait?", Movement Disorders, 21(9): 1419-1424, 2006.

Jacobs et al. "Knee Trembling During Freezing of Gait Represents Multiple Anticipatory Postural Adjustments", Experimental Neurology, 215(2): 334-341, Feb. 2009.

Kammerlind et al. "Effects of Balance Training in Elderly People With Nonperipheral Vertigo and Unsteadiness", Clinical Rehabilitation, 15: 463-470, 2001.

Lim et al. "Effects of External Rhythmical Cueing on Gait in Patients With Parkinson's Disease: A Systematic Review", Clinical Rehabilitation, 19(7):695-713, Jul. 2005.

Liu-Ambrose et al. "Resistance and Agility Training Reduce Fall Risk in Women Aged 75 to 85 With Low Bone Mass: A 6-Month Randomized, Controlled Trial", Journal of the American Geriatrics Society, 52(5): 657-665, May 2004.

Lord "Aging and Falls: Causes and Prevention", Journal of Musculoskeletal and Neuronal Interaction, 7(4): 347, 2007.

Lord et al. "Choice Stepping Reaction Time: A Composite Measure of Falls Risk in Older People", Journal of Gerontology, 56A(10): M627-M632, 2001.

Lord et al. "Home Environment Risk Factors for Falls in Older People and the Efficacy of Home Modifications", Age and Ageing, 35(2): ii55-ii59, 2006.

(56) References Cited

OTHER PUBLICATIONS

Mehrholz et al. "Treadmill Training for Patients With Parkinson's Disease (Review)", The Cochrane Collaboration, The Cochrane Library, 1: 1-31, 2010.
Menz et al. "A Structural Equation Model Relating Impaired Sensorimotor Function, Fear of Falling and Gait Patterns in Older People", Gait & Posture, 25: 243-249, 2007.
Mirelman et al. "Virtual Reality for Gait Training: Can it Induce Motor Learning to Enhance Complex Walking and Reduce Fall Risk in Patients With Parkinson's Disease?", The Journals of Gerontology, Series A, Biological Sciences and Medical Sciences, 66(2): 234-240, Feb. 28, 2011.
Moore et al. "Ambulatory Monitoring of Freezing of Gait in Parkinson's Disease", Journal of Neuroscience Methods, 167: 340-348, Jan. 30, 2008.
Nieuwboer et al. "Abnormalities of the Spatiotemporal Characteristics of Gait at the Onset of Freezing in Parkinson's Disease", Movement Disorders, 16(6): 1066-1075, 2001.
Nieuwboer et al. "Electromyographic Profiles of Gait Prior to Onset of Freezing Episodes in Patients With Parkinsons's Disease", Brain, 127(7): 1650-1660, 2004.
Nieuwboer et al. "Reliability of the New Freezing of Gait Questionnaire: Agreement Between Patients With Parkinson's Disease and Their Carers", Gait & Posture, 30: 459-463, 2009.
Nutt et al. "Freezing of Gait: Moving Forward on a Mysterious Clinical Phenomenon", The Lancet Neurology, 10: 734-744, 2011.
Nyberg et al. "Development of a Virtual Reality System to Study Tendency of Falling Among Older People", Proceedings of the 5th International Conference on Disability, Virtual Reality and Associated Technologies, ICDVRAT 2004, Oxford, UK, Sep. 20-22, 2004, p. 315-320, Sep. 22, 2004.
Park et al. "Development of a VR-Based Treadmill Control Interface for Gait Assessment of Patients With Parkinson's Disease", 2011 IEEE International Conference on Rehabilitation Robotics, Rehab Week Zurich, ETH Zurich Science Sity, Switzerland, Jun. 29-Jul. 1, 2011, p. 1-5, Jul. 1, 2011.
Plotnik et al. "Bilateral Coordination of Walking and Freezing of Gait in Parkinson's Disease", Europeam Journal of Neuroscience, 27: 1999-2006, 2008.
Plotnik et al. "Is Freezing of Gait in Parkinson's Disease Related to Asymmetric Motor Function", Annals of Neurology, 57(5): 656-663, May 2005.
Plotnik et al. "The Role of Gait Rhythmicity and Bilateral Coordination of Stepping in the Pathophysiology of Freezing of Gait in Parkinson's Disease", Movement Disorders, 23(2): S444-S450, 2008.
Rochester et al. "Targeting Dopa-Sensitive and Dopa-Resistant Gait Dysfunction in Parkinson's Disease: Selective Responses to Internal and External Cues", Movement Disorders, 23(3): 430-435, 2011.
Rubinstein et al. "The Power of Cueing to Circumvent Dopamine Deficits: A Review of Physical Therapy Treatment of Gait Disturbances in Parkinson's Disease", Movement Disorders, 17(6): 1148-1160, 2002.
Schaafsma et al. "Characterization of Freezing of Gait Subtypes and the Response of Each to Levodopa in Parkinson's Disease", European Journal of Neurology, 10: 391-398, 2003.
Snijders et al. "Clinimetrics of Freezing of Gait", Movement Disorders, 23(2): S468-S474, 2008.
Snijders et al. "Cycling for Freezing of Gait", The New England Journal of Medicine, 362: e46, Apr. 1, 2010.
Spildooren et al. "Freezing of Gait in Parkinson's Disease: The Impact of Dual-Tasking and Turning", Movement Disorders, 25(15): 2563-2570, 2010.

St George et al. "Sleep Quality and Falls in Older People Living in Self-And Assisted-Care Villages", Gerontology, 55: 162-168, 2009.
Thurman et al. Practice Parameter: Assessing Patients in a Neurology Practice for Risk of Falls (An Evidence-Based Review): Report of the Quality Standards Subcommittee of the American Academy of Neurology, Neurology, 70: 473-479, 2008.
Verghese et al. "Validity of Divided Attention Tasks in Predicting Falls in Older Individuals: A Preliminary Study", Journal of the American Geriatrics Society, 50(9): 1572-1576, Sep. 2002.
Visser et al. "The Clinical Utility of Posturography", Clinical Neurophysiology, 119: 2424-2436, 2008.
Voukelatos et al. "A Randomized, Controlled Trial of tai chi for the Prevention of Falls: The Central Sydney tai chi Trial", Journal of the American Geriatrics Society, 55(8): 1185-1191, 2007.
Walker et al. "Virtual Reality-Enhanced Partial Body Weight-Supported Treadmill Training Poststroke: Feasibility and Effectiveness in 6 Subjects", Archives of Physical Medicine and Rehabilitation, 91(1): 115-122, Jan. 2010.
Whitney et al. "Streamlining Assessment and Intervention in a Falls Clinic Using the Timed Up and Go Test and Physiological Profile Assessments", Age and Ageing, 34: 567-571, 2005.
Ziegler et al. "A New Rating Instrument to Assess Festination and Freezing Gait in Parkinsonian Patients", Movement Disorders, 25(8): 1012-1018, 2010.
Supplementary European Search Report and the European Search Opinion dated May 19, 2015 From the European Patent Office Re. Application No. 12839495.4.
Hanakawa et al. "Enhanced Lateral Premotor Activity During Paradoxical Gait in Parkinson's Disease", Annals of Neurology, XP055188096, 45(3): 329-336, Mar. 1, 1999. p. 329, r-h Col., Last Para—p. 333, r-h Col., Para 1, Figs.
Maidan et al. "Doeas Heart Rate Change With Freezing of Gait in Patients With Parkinson's Disease?", Parkinsonism and Related Disorders, XP026909427, 16(Suppl.1): S39-S40, #136, Feb. 1, 2010. Abstract No. 136, p. S39, r-h Col.—p. S40, 1-h Col.
Yang et al. "Vitruality Reality-Based Training Improves Community Ambulation in Individuals With Stroke: A Randomized Controlled Trial", Gait & Posture, XP022940963, 28(2): 201-206, Aug. 1, 2008. p. 202, r-h col., Para 1—p. 203, 1-h Col., Para 2.
International Preliminary Report on Patentability dated Apr. 24, 2014 From the International Bureau of WIPO Re. Application No. PCT/IB2012/055453.
Official Action dated Apr. 20, 2016 From the US Patent and Trademark Office Re. U.S. Appl. No. 14/350,569.
Restriction Official Action dated Jan. 25, 2016 From the US Patent and Trademark Office Re. U.S. Appl. No. 14/350,569.
Official Action dated Sep. 2, 2016 From the U.S. Patent and Trademark Office Re. U.S. Appl. No. 14/350,569.
Official Action dated Mar. 21, 2018 From the U.S. Patent and Trademark Office Re. U.S. Appl. No. 15/607,548. (22 pages).
Official Action dated Jun. 8, 2017 From the U.S. Patent and Trademark Office Re. U.S. Appl. No. 14/350,569. (7 pages).
Applicant-Initiated Interview Summary dated Sep. 28, 2017 From the US Patent and Trademark Office Re. U.S. Appl. No. 14/350,569. (3 pages).
Office Action dated Sep. 18, 2017 From the Israel Patent Office Re. Application No. 231996 and its Translation Into English. (6 Pages).
Restriction Official Action dated Sep. 27, 2017 From the US Patent and Trademark Office Re. U.S. Appl. No. 15/607,548. (4 pages).
Official Action dated Aug. 8, 2018 From the U.S. Patent and Trademark Office Re. U.S. Appl. No. 15/607,548. (8 pages).
Requisition by the Examiner dated Jul. 30, 2018 From the Innovation, Science and Economic Development Canada, Canadian Intellectual Property Office Re. Application No. 2,851,443. (7 Pages).
Office Action dated May 31, 2018 From the Israel Patent Office Re. Application No. 231996 and its Translation Into English. (4 Pages).

* cited by examiner

| Table 1: Fall risk quantification and scoring. | | |
|---|---|---|
| Score | Level | Description |
| 0 | No risk | |
| 1 | Low fall risk | Changes in gait pattern were rare or only with high complexity tasks or environments. Gait dynamics within normal range |
| 2 | Moderate fall risk | Occasional changes in gait pattern, could be in low complex environments, while attention is distracted, or as a result of provocation. Gait dynamics are slightly abnormal |
| 3 | High fall risk | Frequent changes in gait pattern or detected missteps even with low level provocation, simple environments and cognitive challenges. High gait variability and asymmetry. |

FIG. 6

| Table 2: Subjects characteristics | | | | | |
|---|---|---|---|---|---|
| Subject Number | Age (y) | Gender | Falls (per year) | MOCA | Gait speed (m/s) |
| 1 | 83 | F | 2 | 25 | 1.4 |
| 2 | 67 | M | 0 | 27 | 1.4 |
| 3 | 68 | F | 2 | 26 | 1.3 |
| 4 | 69 | M | 4 | 27 | 1.5 |
| Mean ± SD | 71.7±7.5 | 50 F% | 2±1.6 | 26.7±1.7 | 1.4±0.1 |

FIG. 7

| Table 3: Measures of consistency | | | | |
|---|---|---|---|---|
| Subject | Amplitude (prs) | Width (prs) | CV (%) | PCI (%) |
| 1 | 0.34±0.01 | 1.09±0.20 | 1.83% | 2.01% |
| 2 | 0.44±0.02 | 0.95±0.005 | 0.84% | 1.41% |
| 3 | 0.25±0.05 | 1.9±0.60 | 1.62% | 6.14% |
| 4 | 0.10±0.001 | 1.4±0.81 | 4.01% | 3.98% |
| | (higher values reflect more consistency) | (lower values reflect less consistency) | (lower values reflect greater rhythmicity) | (lower values reflect more left-right consistency) |

FIG. 9

| Table 4: Subject 1- testing parameters | | | | | | |
|---|---|---|---|---|---|---|
| | Trial 1- difficult | Trail 2- moderate | Trial 3 - environment | Trial 4 - Gait challenges | Trial 5- Cognitive | Total |
| Gait speed | 1.40 | 1.40 | 1.40 | 1.40 | 1.40 | 1.40 |
| TM speed | 1.20 | 1.20 | 1.20 | 1.20 | 1.20 | 1.20 |
| event detected | 1.00 | 1.00 | 0.00 | 0.00 | 1.00 | 3.00 |
| event Researcher | 1.00 | 0.00 | 0.00 | 0.00 | 1.00 | 2.00 |
| event on video | 1.00 | 0.00 | 0.00 | 0.00 | 1.00 | 2.00 |
| Event due to provocation | 1-tunnel | 0 | 0 | 0 | | 1 |
| obstacles passed | 12.00 | 19.00 | 20.00 | 0.00 | 12.00 | 63.00 |
| obstacles failed | 16.00 | 14.00 | 13.00 | 0.00 | 27.00 | 70.00 |
| hurdles | 8.00 | 6.00 | 7.00 | 0.00 | 12.00 | 33.00 |
| puddles | 8.00 | 7.00 | 6.00 | 0.00 | 15.00 | 36.00 |
| Cost environment | // | // | 1.49 | 1.64 | // | 0.15 |
| Cost DT | // | // | // | 1.64 | 0.74 | 0.9 |
| width of dominant frq | // | // | // | 1.09 | // | 1.09 |
| Symmetry ratio | // | // | // | // | // | 98.00 |
| PCI | // | // | // | // | // | 2.01 |
| Fall risk score | // | // | // | // | // | 1 |

FIG. 15

| Table 5: Subject 2 testing parameters | | | | | | |
|---|---|---|---|---|---|---|
| | Trial 1 - difficult | Trial 2 - moderate | Trial 3 - environment | Trial 4 - Gait challenges | Trial 5 - Cognitive | Total |
| Gait speed | 1.4 | 1.4 | 1.4 | 1.4 | 1.4 | 1.4 |
| TM speed | 1.2 | 1.2 | 1.2 | 1.2 | 1.2 | 1.2 |
| event detected | 2.0 | 0.0 | 1.0 | 0.0 | 2.0 | 5.0 |
| event Researcher | 0.0 | 0.0 | 0.0 | 0.0 | 2.0 | 2.0 |
| event on video | 0.0 | 0.0 | 0.0 | 0.0 | 2.0 | 2.0 |
| Event due to provocation | 1-tunnel | 0 | 0 | 0 | 0 | |
| obstacles passed | 14.0 | 13.0 | 14.0 | 0.0 | 18.0 | 59.0 |
| obstacles failed | 17.0 | 11.0 | 14.0 | 0.0 | 18.0 | 60.0 |
| hurdles | 4.0 | 5.0 | 11.0 | 0.0 | 15.0 | 35.0 |
| puddles | 3.0 | 6.0 | 3.0 | 0.0 | 3.0 | 15.0 |
| Cost environment | // | // | 1.44 | 1.59 | // | -0.15 |
| Cost DT | // | // | // | 1.59 | 1.66 | 0.07 |
| width of dominant frq | // | // | // | 0.95 | // | 0.95 |
| Symmetry ratio | // | // | // | // | // | 99.0 |
| PCI | // | // | // | // | // | 1.41 |
| Fall risk score | // | // | // | // | // | 1.0 |

FIG. 16

| Table 6: Subject 3 testing parameters | | | | | | |
|---|---|---|---|---|---|---|
| | Trial 1 - difficult | Trail 2 - moderate | Trial 3 - environment | Trial 4 - Gait challenges | Trial 5 - Cognitive | Total |
| Gait speed | 1.2 | 1.2 | 1.2 | 1.2 | 1.2 | 1.2 |
| TM speed | 1.0 | 1.0 | 1.0 | 1.0 | 1.0 | 1.0 |
| event detected | 2 | 2 | 1 | 0 | 2 | 7.0 |
| event Researcher | 2 | 1 | 1 | 0 | 2 | 6.0 |
| event on video | 2 | 1 | 1 | 0 | 2 | 6.0 |
| Event due to provocation | 2- tunnel, bridge | bridge | cave | 0 | cave | 5.0 |
| obstacles passed | 3 | 7 | 8 | 0 | 9 | 27.0 |
| obstacles failed | 38 | 27 | 24 | 0 | 29 | 118.0 |
| hurdles | 20 | 16 | 17 | 0 | 17 | 70.0 |
| puddles | 18 | 11 | 7 | 0 | 12 | 48.0 |
| Cost environment | // | // | 0.76 | 0.8 | // | 0.10 |
| Cost DT | // | // | // | 0.8 | 0.72 | 0.10 |
| width of dominant frq | // | // | // | 1.91 | // | 1.91 |
| Symmetry ratio | | | | | | 50% |
| PCI | | | | | | 6.14 |
| Fall risk score | | | | | | 3.0 |

FIG. 17

| Table 7 : Subject 4 testing parameters | | | | | | |
|---|---|---|---|---|---|---|
|  | Trial 1- difficult | Trail 2- moderate | Trial 3 - environment | Trial 4 - Gait challenges | Trial 5- Cognitive | Total |
| Gait speed | 1.4 | 1.4 | 1.4 | 1.4 | 1.4 | 1.4 |
| TM speed | 1.2 | 1.2 | 1.2 | 1.2 | 1.2 | 1.2 |
| event detected | 4 | 3 | 5 | 0 | 4 | 16.0 |
| event Researcher | 3 | 3 | 4 | 0 | 4 | 14.0 |
| event on video | 3 | 2 | 4 | 0 | 4 | 13.0 |
| Event due to provocation | 2-tunnel, bridge | cave | 2-tunnel, cave | 0 | 2-tunnel, bridge | 7.0 |
| obstacles passed | 6 | 18 | 7 | 0 | 16 | 47.0 |
| obstacles failed | 19 | 31 | 17 | 0 | 27 | 94.0 |
| hurdles | 13 | 23 | 10 | 0 | 23 | 69.0 |
| puddles | 6 | 8 | 7 | 0 | 4 | 25.0 |
| Cost environment | // | // | 1.6 | 0.8 | // | -0.9 |
| Cost DT | // | // | // | 0.8 | 1.41 | -1.0 |
| width of dominant frq | // | // | // | 1.4 | // | 1.4 |
| Symmetry ratio | // | // | // | // | // | 98.0 |
| PCI | // | // | // | // | // | 3.98 |
| Fall risk score |  |  |  |  |  | 3.0 |

FIG. 18

VIRTUAL REALITY FOR MOVEMENT DISORDER DIAGNOSIS AND/OR TREATMENT

RELATED APPLICATIONS

PCT Patent Application No. PCT/IB2012/055453 is related to a co-filed PCT Patent Application No. PCT/IB2012/055454, titled: "FREEZING OF GAIT (FOG), DETECTION, PREDICTION AND/OR TREATMENT" the disclosure of which is incorporated herein by reference. In an exemplary embodiment of the invention, provocation and/or training programs as described therein are presented using methods and apparatus as described herein.

This application is a National Phase of PCT Patent Application No. PCT/IB2012/055453 having International filing date of Oct. 9, 2012, which claims the benefit of priority also under 35 USC 119(e) of U.S. Provisional Patent Application Nos. 61/545,164 and 61/545,161, both filed on Oct. 9, 2011. The contents of the above applications are all incorporated by reference as if fully set forth herein in their entirety.

FIELD AND BACKGROUND OF THE INVENTION

The present invention, in some embodiments thereof, relates to diagnosing, monitoring and/or treating persons with a fall risk and/or other pathological conditions.

Falls are a leading cause of morbidity and mortality among older adults and have a tremendous impact on health care economics, social function, and quality of life. Gait impairments and falls are ubiquitous among older adults and patients with common neurological diseases. Approximately 30% of community-dwelling adults over the age of 65 fall at least once a year. The consequences of these falls may be severe, leading to institutionalization, loss of functional independence, disability, fear of falling, depression and social isolation. Attending to this problem is of great importance as the aging population in the world is continuously growing, and expected to double by the year 2030, reaching 70 million older adults over the age of 65.

In the year 2000 there were approximately 35 million adults aged 65 years and older in the US. By the year 2030 the older population may reach 70 million. According to figures released in 2006 by the United States Center for Disease Control and Prevention (CDC), about 5.8 million (15.9%) persons aged 65 years and older reported falling at least once during just a three month period, and 1.8 million (31.3%) of those who fell sustained an injury that resulted in a doctor visit or restricted activity for at least one day. In the elderly population, falls are the leading cause for disability and loss of independence. The CDC recently estimated that 19 billion dollars were spent on non-fatal fall related injuries in the year 2000 alone. Similar relative numbers have been reported in Europe and in Israel. The health care dollars spent on falls in the west is only expected to rise as the number of older adults continues to increase. But even when there is no physical injury, a fall often produces fear of falling, social isolation, and self-imposed restrictions in activities of daily living that may further increase fall risk and curtail independence.

Most falls occur during walking and, not surprisingly, gait impairments have been associated with an increased risk of falls. Gait abnormalities in elderly fallers include reduced gait speed, stride length, and increased stride symmetry. Fear of falling, a cautious gait, gait unsteadiness, or inconsistency and dysrhythmicity of stepping have been recognized as mediators of fall risk. Another risk factor identified as a cause for falls in the elderly is obstacle crossing abilities. Compared to healthy young adults, older adults walk more slowly during obstacle crossing, with smaller steps landing dangerously closer to the obstacle with their lead limb. Age-related deficits in vision, proprioception, visual-spatial orientation, and attention can also negatively impact postural stability and lower limb kinematics when crossing obstacles.

During the past two decades, much research on falls has focused on determining "intrinsic" and "extrinsic" risk factors.

While there are many motor changes that contribute to fall risk, these changes do not always adequately explain the magnitude of this incidence. There is a growing body of research that specifically links the cognitive sub-domains of attention and executive function (EF) to gait alterations and fall risk, especially dual task ability. EF and attentional reserves are reduced with ageing. This reduction places older adults at a heightened risk of falling when they attempt to perform two or more tasks simultaneously, even if the tasks are otherwise considered to be automatic or demand minimal attention.

Over the past two decades, tremendous advances have been made in the understanding of the factors that contribute to falls and many multi-factorial interventions have been developed[1-11]. Unfortunately, however, because of limited health care dollars, current clinical consensus suggests reserving these interventions for people with a high fall risk[2], 3. This requires the ability to predict future falls and quantify fall risk. Thus, because of the tremendous impact of falls on functional independence, health care economics, and quality of life, much effort has been devoted to the development and evaluation of optimal measures of fall risk[3], 12-21.

Various systems have been proposed to automatically identify falls, so that an action can be triggered to help alleviate the damage caused by the fall. However detecting falls upon occurrence can only provide a solution for treatment or alerting help. Few solutions have been identified for the detection of individuals at risk of falls before the actual first fall. These tend to include a uni-dimensional medical assessment of balance and mobility function that is usually done in a doctor's office or a laboratory setting under less than normal conditions.

Interventions designed to reduce the risk of falls have also been developed and tested. More recently, however, specific forms of exercise have been recommended as elements of fall-prevention programs for older adults. For example, aerobic-type exercises and exercises that target balance, strength and gait are common elements of multifactorial fall prevention interventions. Typically, these exercises report a reduction in fall risk by only about 10% to 20% and are not yet optimal.

A large and rapidly increasing number of randomized controlled trials investigating the effectiveness of fall-preventive options have been published over the last decade. Many preventive intervention programs based on reported risk factors have been proposed and evaluated. These have included exercise programs to improve strength or balance, education programs, medication optimization, and environmental modification. Most exercise programs have focused on training the individual and attempted to improve and impairment that caused the increased risk. Earlier reviews suggested that multi-factorial interventions that combine both motor and cognitive tasks to enhance stability and improve dual tasking abilities in the elderly population may be among the most effective, and the American Geriatrics Society and British Geriatrics Society recommended this approach as a primary treatment strategy in their guideline for prevention of falls. To date, however, there is no consensus as to the efficacy, type of intervention, frequency or intensity of the intervention that can be widely used and readily reproduced for successful prevention of falls.

Additional background art includes the addressing fall risk. Subsensory vibratory noise provided by insoles containing vibrating actuators was used for reducing gait variability in a population of elderly recurrent fallers[22]. Results were modest and with no long term effect. The vibratory insoles can provide only treatment; once individuals at risk are identified they can be treated with this device in a task specific manner to address gait variability and stability. Another technological device used to address fall risk is the Balance master (SMART EquiTest) which provides both an objective assessment of balance control and postural stability under dynamic test conditions and can also be used for training. Evidence has shown some improvement in balance after using this approach[23].

REFERENCE LIST (1) Rizzo J A, Baker D I, McAvay G, Tinetti M E. The cost-effectiveness of a multifactorial targeted prevention program for falls among community elderly persons. *Med Care* 1996; 34(9):954-69.
(2) Ganz D A, Bao Y, Shekelle P G, Rubenstein L Z. Will my patient fall? *JAMA* 2007; 297(1):77-86.
(3) AGS Guidelines. Guideline for the prevention of falls in older persons. American Geriatrics Society, British Geriatrics Society, and American Academy of Orthopaedic Surgeons Panel on Falls Prevention. *J Am Geriatr Soc* 2001; 49(5):664-72.
(4) Liu-Ambrose T, Khan K M, Eng J J, Janssen P A, Lord S R, McKay H A. Resistance and agility training reduce fall risk in women aged 75 to 85 with low bone mass: a 6-month randomized, controlled trial. *J Am Geriatr Soc* 2004; 52(5):657-65.
(5) Lord S R. Aging and falls: causes and prevention. *J Musculoskelet Neuronal Interact* 2007; 7 (4):347.
(6) Lord S R, Fitzpatrick R C. Choice stepping reaction time: a composite measure of falls risk in older people. *J Gerontol A Biol Sci Med Sci* 2001; 56(10):M627-M632.
(7) Lord S R, Menz H B, Sherrington C. Home environment risk factors for falls in older people and the efficacy of home modifications. *Age Ageing* 2006; 35 Suppl 2:ii55-ii59.
(8) Lord S R, Clark R D, Webster I W. Physiological factors associated with falls in an elderly population. *J Am Geriatr Soc* 1991; 39(12):1194-200.
(9) Menz H B, Lord S R, Fitzpatrick R C. A structural equation model relating impaired sensorimotor function, fear of falling and gait patterns in older people. *Gait Posture* 2007; 25(2):243-9.
(10) St George R J, Delbaere K, Williams P, Lord S R. Sleep Quality and Falls in Older People Living in Self- and Assisted-Care Villages. Gerontology 2008.
(11) Voukelatos A, Cumming R G, Lord S R, Rissel C. A randomized, controlled trial of tai chi for the prevention of falls: the Central Sydney tai chi trial. *J Am Geriatr Soc* 2007; 55(8):1185-91.
(12) Herman T, Inbar-Borovsky N, Brozgol M, Giladi N, Hausdorff J M. The Dynamic Gait Index in healthy older adults: The role of stair climbing, fear of falling and gender. *Gait Posture* 2008.
(13) Podsiadlo D, Richardson S. The timed "Up & Go": a test of basic functional mobility for frail elderly persons. *J Am Geriatr Soc* 1991; 39(2):142-8.
(14) Tinetti M E. Performance-oriented assessment of mobility problems in elderly patients. *J Am Geriatr Soc* 1986; 34(2):119-26.
(15) Verghese J, Buschke H, Viola L, Katz M, Hall C, Kuslansky G, Lipton R. Validity of divided attention tasks in predicting falls in older individuals: a preliminary study. *J Am Geriatr Soc* 2002; 50(9):1572-6.
(16) Visser J E, Carpenter M G, van der K H, Bloem B R. The clinical utility of posturography. *Clin Neurophysiol* 2008.
(17) Thurman D J, Stevens J A, Rao J K. Practice parameter: Assessing patients in a neurology practice for risk of falls (an evidence-based review): report of the Quality Standards Subcommittee of the American Academy of Neurology. *Neurology* 2008; 70(6):473-9.
(18) Berg K O, Wood-Dauphinee S L, Williams J I, Maki B. Measuring balance in the elderly: validation of an instrument. *Can J Public Health* 1992; 83 Suppl 2:S7-11.
(19) Delbaere K, Close J C, Menz H B, Cumming R G, Cameron I D, Sambrook P N, March L M, Lord S R. Development and validation of fall risk screening tools for use in residential aged care facilities. *Med J Aust* 2008; 189(4):193-6.
(20) Narayanan M R, Lord S R, Budge M M, Celler B G, Lovell N H. Falls management: detection and prevention, using a waist-mounted triaxial accelerometer. *Conf Proc IEEE Eng Med Biol Soc* 2007; 2007:4037-40.
(21) Whitney J C, Lord S R, Close J C. Streamlining assessment and intervention in a falls clinic using the Timed Up and Go Test and Physiological Profile Assessments. *Age Ageing* 2005; 34(6):567-71.
(22) Galica A M, Kang H G, Priplata A A, D'Andrea S E, Starobinets O V, Sorond F A, Cupples L A, Lipsitz L A. Subsensory vibrations to the feet reduce gait variability in elderly fallers. Gait Posture 2009; 30(3):383-7.
(23) Kammerlind A S, Hakansson J K, Skogsberg M C. Effects of balance training in elderly people with nonperipheral vertigo and unsteadiness. Clin Rehabil 2001; 15(5):463-70.
(24) Exp Neurol. 2009 February; 215(2):334-41. Knee trembling during freezing of gait represents multiple anticipatory postural adjustments. Jacobs J V, Nutt J G, Carlson-Kuhta P, Stephens M, Horak F B.

SUMMARY OF THE INVENTION

A broad aspect of some embodiments of the invention relates to provoking falls and/or other pathological conditions using triggers and/or situations in order to diagnose, monitor and/or treat persons at risk of falling and/or other pathological conditions.

An aspect of some embodiments of the invention relates to a method of fall risk assessment, comprising:
presenting a subject with a plurality of provocations selected to induce a fall or near fall; and
generating a risk assessment based on response of the subject to the provocations.

In an exemplary embodiment of the invention, subject is selected for screening, before any falls occur. Optionally or alternatively, the subject is selected for monitoring. Optionally or alternatively, the assessment is part of a training program. Optionally or alternatively, presenting comprises presenting using virtual reality (VR). Optionally or alternatively, presenting comprises presenting situations of varying complexity. Optionally or alternatively, presenting comprises presenting triggers of varying difficulty, during an ongoing scene presentation. Optionally or alternatively, presenting comprises presenting provocations both expected to induce falls or near falls and those expected not to induce falls or near falls. Optionally or alternatively, presenting comprises presenting dual motor and cognitive tasks.

In an exemplary embodiment of the invention, presenting comprises personalizing the presentation to the subject performance and/or subject clinical history. Optionally or alternatively, the method comprises identifying one or more parameters of a situation and/or a trigger which induce falls or near falls in the patient. Optionally, the method comprises setting up a training program responsive to the identifying. Optionally or alternatively, the method comprises modifying said provocations in response to said identifying.

In an exemplary embodiment of the invention, said provocations visually simulate daily activities of the subject.

An aspect of some embodiments of the invention relates to a method of treating a subject at risk of falling, comprising:

presenting a subject with a plurality of provocations selected to induce a fall or near fall for a plurality of sessions. Optionally, said presenting comprises presenting according to a training plan. Optionally or alternatively, said presenting comprises presenting according to a progress of the subject. Optionally or alternatively, the method comprises presenting the subject with one or both of a knowledge of performance and a knowledge of results, to assist in his training.

An aspect of some embodiments of the invention relates to apparatus for fall and/or near induction and/or near-induction, comprising:

(a) a display;
(b) a controller configured to present one or more provocations calculated to induce a fall or near fall on the display. Optionally, said controller is configured to select said provocations personalized for a particular subject. Optionally or alternatively, said display is a virtual reality (VR) display.

In an exemplary embodiment of the invention, the apparatus comprises a plurality of wearable modules. Optionally, a module is wireless and includes one or both of a sensor and an actuator.

In an exemplary embodiment of the invention, the apparatus comprises a treadmill controlled by said controller.

An aspect of some embodiments of the invention relates to method of assessment of gait pathologies, comprising:

presenting a subject with a plurality of provocations selected to induce the occurrence of a pathological behavior; and generating a risk assessment based on response of the subject to the provocations. In an exemplary embodiment of the invention, said presenting is under conditions where the subject is not likely to hurt himself by said occurrence.

There is provided in accordance with an exemplary embodiment of the invention a method of fall risk assessment, comprising:

presenting a subject with a plurality of provocations selected to induce a fall or near fall; and generating a risk assessment based on response of the subject to the provocations. Optionally, said generating is based only on near-falls.

In an exemplary embodiment of the invention, said generating is based on at least one fall.

In an exemplary embodiment of the invention, the subject is selected for screening, before any falls occur.

In an exemplary embodiment of the invention, the subject is selected for monitoring.

In an exemplary embodiment of the invention, the assessment is part of a training program.

In an exemplary embodiment of the invention, presenting comprises presenting using virtual reality (VR).

In an exemplary embodiment of the invention, presenting comprises presenting situations of varying complexity.

In an exemplary embodiment of the invention, presenting comprises presenting triggers of varying difficulty, during an ongoing scene presentation.

In an exemplary embodiment of the invention, presenting comprises presenting provocations both expected to induce falls or near falls and those expected not to induce falls or near falls.

In an exemplary embodiment of the invention, presenting comprises presenting dual motor and cognitive tasks.

In an exemplary embodiment of the invention, presenting comprises personalizing the presentation to the subject performance and/or subject clinical history.

In an exemplary embodiment of the invention, the method comprises identifying one or more parameters of a situation and/or a trigger which induce falls or near falls in the patient. Optionally, the method comprises setting up a training program responsive to the identifying. Optionally or alternatively, the method comprises modifying said provocations in response to said identifying.

In an exemplary embodiment of the invention, said provocations visually simulate daily activities of the subject.

In an exemplary embodiment of the invention, the method comprises detecting a near fall based on a change in the pattern of data from one or more movement sensors, with the support of one or more additional physiologic sensors.

In an exemplary embodiment of the invention, the method comprises detecting a fall or near fall in a person having fewer than 1 falls or near falls in 10,000 steps in daily life.

In an exemplary embodiment of the invention, increasing a rate of falls or near falls over average daily activities by a factor of at least 10.

In an exemplary embodiment of the invention, increasing a rate of falls or near falls over average daily activities by a factor of at least 100.

There is provided in accordance with an exemplary embodiment of the invention a method of treating a subject at risk of falling, comprising:

presenting a subject with a plurality of provocations selected to induce a fall or near fall for a plurality of sessions. Optionally, said presenting comprises presenting according to a training plan.

In an exemplary embodiment of the invention, said presenting comprises presenting according to a progress of the subject.

In an exemplary embodiment of the invention, the method comprises presenting the subject with one or both of a knowledge of performance and a knowledge of results, to assist in his training.

There is provided in accordance with an exemplary embodiment of the invention apparatus for fall and/or near induction and/or near-induction, comprising:

(a) a display;
(b) a controller configured to present one or more provocations calculated to induce a fall or near fall on the display. Optionally, said controller is configured to select said provocations personalized for a particular subject. Optionally, said controller is configured to select said provocations in response to measurement by the system of subject activity. Optionally or alternatively, said controller is configured to modify a parameter of a selected provocation in response to measurement by the system of subject activity. Optionally, said modification comprises the controller selecting a provocation which matches a weakness of the subject, detected by analysis of said measurement.

In an exemplary embodiment of the invention, said display is a virtual reality (VR) display.

In an exemplary embodiment of the invention, the apparatus comprises a plurality of wearable modules. Optionally, a module is wireless and includes one or both of a sensor and an actuator.

In an exemplary embodiment of the invention, the apparatus comprises a treadmill controlled by said controller.

In an exemplary embodiment of the invention, said controller is configured to detect a fall and a near fall. Optionally, said detection is based, at least in part, on a relationship between the power in normal gait frequencies and abnormal gait frequencies, in an acceleration signal. Optionally or alternatively, said detection is based, at least in part using a machine learning classification method. Optionally or alternatively, said detection is based, at least in part, on one or both of a heart rate and an indication of frontal lobe activity.

In an exemplary embodiment of the invention, said controller is configured to measure at least an indication of brain activity.

In an exemplary embodiment of the invention, said controller is configured to calculate a fall risk score.

In an exemplary embodiment of the invention, said controller is configured to select said provocations in response to a treatment plan for said subject.

There is provided in accordance with an exemplary embodiment of the invention a method of assessment of one or more gait pathologies, comprising:

presenting a subject with a plurality of provocations selected to induce the occurrence of a pathological behavior; and generating a risk assessment based on response of the subject to the provocations. Optionally, said presenting is under conditions where the subject is not likely to hurt himself by said occurrence. Optionally, said assessment is based on change of activity in frontal lobes of the subject. Optionally, said change in activity is detected using EEG.

In an exemplary embodiment of the invention, an increase in blood flow to a frontal lobe is taken to indicate a gait disorder due to lack or over activity in the frontal lobes.

In an exemplary embodiment of the invention, a decrease in blood flow to a frontal lobe is taken to indicate a gait disorder due to frontal lobe dysfunction.

In an exemplary embodiment of the invention, said risk assessment is based also on a background measurement of the patient.

In an exemplary embodiment of the invention, said provocation includes one or more of a cognitive load, a perceptual load and a motor load.

In an exemplary embodiment of the invention, said presenting comprises presenting while the patient is on a locomotion device.

There is provided in accordance with an exemplary embodiment of the invention a method of treating a gait disorder, comprising:

measuring one or more physiological parameters of a subject during locomotion;

automatically determining a weakness of said subject with respect to gait normality, based on said measuring; and providing provocation based training to said subject based on said determining. Optionally, said physiological parameter includes an APA.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 shows a table 1 of fall risk quantization and scoring, in accordance with exemplary embodiments of the invention;

FIG. 7 shows a table 2 of subject characteristics, in accordance with exemplary embodiments of the invention;

FIG. 9 shows a table 3 of measurements of consistency, in accordance with exemplary embodiments of the invention;

FIG. 15 shows a table 4 of testing parameters of subject 1, in accordance with exemplary embodiments of the invention;

FIG. 16 shows a table 5 of testing parameters of subject 2, in accordance with exemplary embodiments of the invention;

FIG. 17 shows a table 6 of testing parameters of subject 3, in accordance with exemplary embodiments of the invention; and FIG. 18 shows a table 7 of testing parameters of subject 4, in accordance with exemplary embodiments of the invention.

DESCRIPTION OF SPECIFIC EMBODIMENTS OF THE INVENTION

Figure 1:
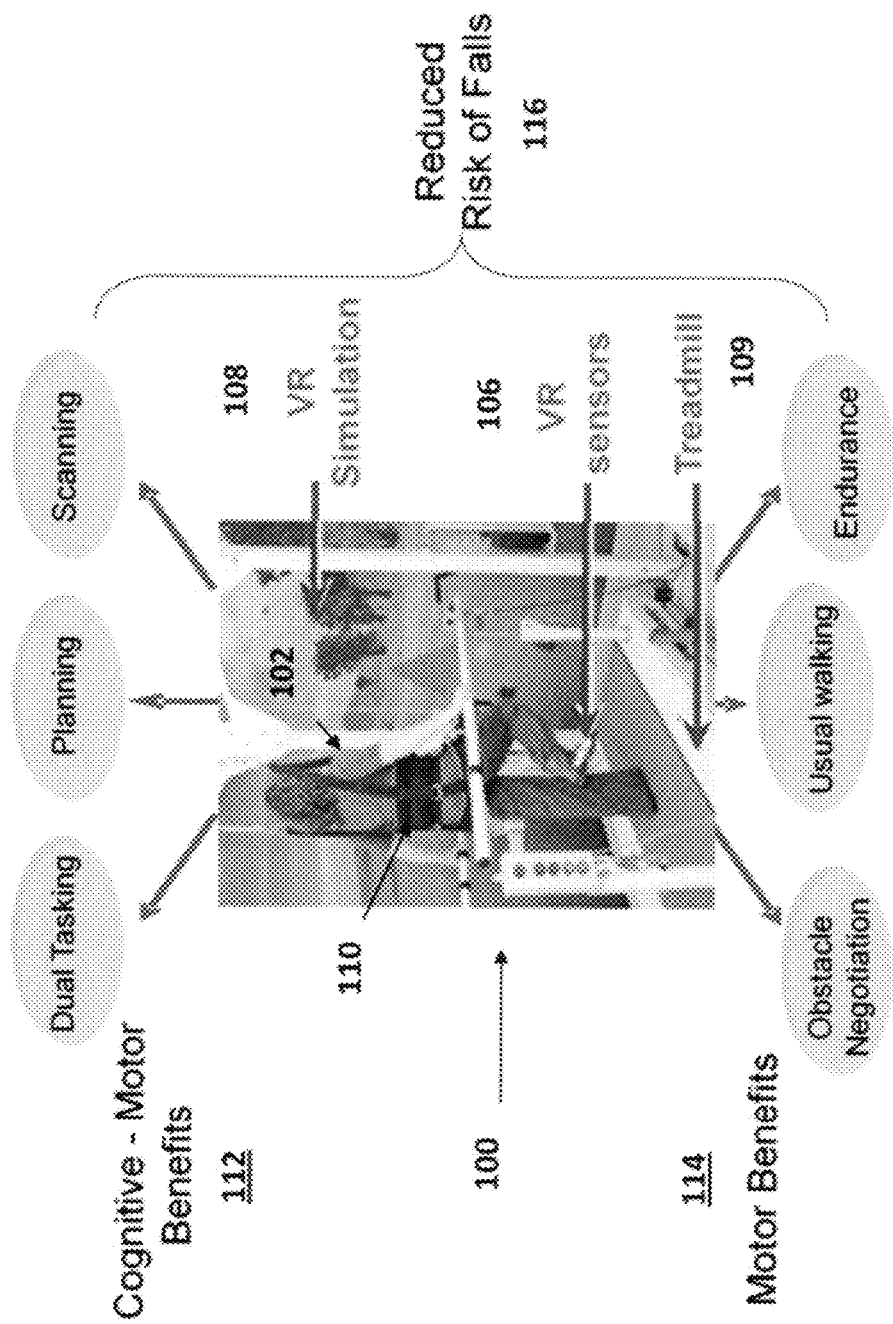
FIG. 1 is a schematic diagram of a VR-based system in accordance with exemplary embodiments of the invention.

The present invention, in some embodiments thereof, relates to diagnosing, monitoring and/or treating persons with a fall risk and/or other pathological conditions.

Overview

Some embodiments of the invention make use of the realization that gait as well as obstacle negotiation heavily relies on the availability of ample cognitive resources, due to the need for motor planning and visually dependent gait regulation. There is a growing body of research that specifically links the cognitive sub-domains of attention and executive function (EF) to gait alterations and fall risk. EF apparently plays a critical role in the regulation of gait especially under challenging conditions where decisions need to be made in real-time such as walking while avoiding obstacles and walking while simultaneously performing another task, i.e., dual tasking (DT). This may explain why falls occur so frequently among older adults, as many older adults suffer from age-associated decline in cognitive function, even though they have not reached the level of "cognitive impairment". In fact, it has been recently shown that EF scores and dual tasking gait performance may predict future falls during 2-years of follow-up among otherwise healthy older adults who reported no falls in the year prior to the study (Herman et al 2010). The use of EF neuropsychological tests to predict future falls allows us to identify a population at risk.

The present invention, in some embodiments thereof, takes this knowledge one step forward by using a test setting which presents motor and/or cognitive challenges in a manner which may unmask compensatory strategies and/or detect risk of falls and/or other gait disorders in a wider population base, not only those who have mild or minimal cognitive impairments but also in individuals that would not show signs in clinical testing. In some embodiments, the test can detect subtle signs of gait impairment, possibly before they would otherwise be manifest. While some signs of diminished performance in high challenging tasks may be observed in almost all individuals, in an exemplary embodiment of the invention, it is the pattern of movement and the cumulative information regarding the performance on these tasks that is used quantify fall risk and/or risk of other gait impairment. For example, a person may have many mistakes on an obstacle navigation task but his gait pattern may not suffer and vice versa suggesting sufficient compensatory strategies to enable recovery from missteps and therefore a low or no-risk of falls.

Since falls are episodic by nature and are most likely the result of a failure of multiple systems, it has been considered difficult to quantitatively assess the risk of a person and their propensity towards falls. Missteps or trips have been identified as "mini-falls" that did not result in a fall either because the person was able to recover or because the loss of balance or trip did not reach enough power and might have been considered to imply a higher risk for falls. However, identifying missteps (and falls for that matter) requires relying on the person's self report, which may not be sufficiently reliable (especially among older adults with problems of memory and recall).

In an exemplary embodiment of the invention, there is provided a reliable method that will identify potential "fallers", possibly prior to the first fall, which usually starts the vicious cycle that is difficult to escape from. It is expected that early intervention, before the first fall, will be much more efficacious and cost effective, however, the challenge, answered by some embodiments of the invention, is to identify persons with an increased fall risk in this relatively early stage.

In accordance with exemplary embodiments of the invention, an adaptive system is provided which may allow for one or more of accurate diagnosis of the risk for falls, quantifying the severity of fall risk and/or providing treatment that will be personalized and/or tailored for the person's needs in order to improve functional ability, lower the risk of falls and/or maintain health. In an exemplary embodiment of the invention, an all-in-one system is provided which uses virtual reality technology to introduce challenges and a tailored "stress test" that may otherwise cause falls, but in a safe environment. The use of a 'closed loop' system enables the unmasking of fall risk that may not be noticeable in normal conditions when compensatory strategies can be used. Once fall risk is detected and quantified, an appropriate treatment can be delivered.

In an exemplary embodiment of the invention, such technology provides a feasible and usable system for diagnosing and quantifying fall risk, for example, assess the possibility of using the system to identify individuals with risk of falls, using, for example, the algorithms described herein, but not limited thereto, optionally using one or more physiological measures (e.g., simple, such as heart rate or processed, such as APAs). In an exemplary embodiment of the invention, there is provided a method to quantify the risk for falls by combining different parameters of performance provided by a system as described herein or other systems. As noted below, the system, in accordance with some embodiments of the invention can be utilized for therapeutic purposes, for example, by providing the appropriate exposure to circumstances that are most likely to lead to falls in a given individual. In an exemplary embodiment of the invention, the rate (e.g., per step) of falls, missteps and/or other gait abnormalities are increased by the system, optionally in a controlled manner, by a factor of, for example, 5, 10, 50, 100, 300, 1000 or greater or intermediate factors.

An aspect of some embodiments of the invention relates to using various display technologies so as to provoke falls and/or near falls in people, e.g., a "gait" or "fall" stress test. In an exemplary embodiment of the invention, the provocation is selected to use specific triggers and/or situations. In an exemplary embodiment of the invention, the triggers are selected to have different intensities so as to estimate susceptibility to falling. Optionally or alternatively, the triggers are selected to be of different types so as to provide an indication of the types of situations where falls are more likely and/or to help identify particular individual or sets of deficits in a patient, which predispose the patient to falling. Optionally, such deficits are then treated, for example, using training, optionally using a same system design and/or triggers and/or situations, as used for diagnosis.

In an exemplary embodiment of the invention, the provocations (challenges) are applied/modified (e.g., type, frequency, intensity) using a closed loop with respect to the effect of previous challenges and/or using an open loop, with respect to desired diagnosis.

In an exemplary embodiment of the invention, such a 'fall risk stress test' based on physiological measures is optionally used to quantify such risks to assess characteristics of the gait disorder of a particular individual and/or match up the individual to a stereotype of a known gait disorder behavior, optionally with an associated suggested treatment, prognosis and/or daily living advice.

As also shown below, initial studies using some embodiments of the invention show the ability of a VR system in accordance with some embodiments of the invention to provoke and/or detect gait changes and/or fall risk under safe environmental conditions. For example, an exemplary system was able to provoke missteps on the treadmill and to sensitively detect these events. Further, an optional a fall risk score that may be used to provide care to individuals with a high risk for falling is quantified based on such detection.

In an exemplary embodiment of the invention, the score is a linear sum of considerations, each weighted, for example, according to patient characteristics, for example, based on a library of control subjects. Other forms of score formula may be used as well.

In an exemplary embodiment of the invention, efficacy of treatment and/or changes (or stability) in patient risk, are monitored by periodic (or other) testing of the patient using the diagnosis system.

The identification of individuals who are at risk of falls is based to date mainly on assessing biomechanical structures and medical problems such as balance disorders, weakness, visual deficits and neurological or orthopedic impairments. However these deficits only cover a small portion of the percent of falls in aging.

It is a particular feature of some embodiments of the invention that "provocation" of difficult situations that may cause falls in the elderly is provided and/or used for detecting a threshold that beyond it a person may fall, optionally specifically targeting the cognitive-motor interactions that are critical to fall risk.

It is a particular feature of some embodiments of the invention that the display technologies used provide a virtual reality (VR) to the patient. This allows, for example, for various situations to be more easily tried out on a patient. Optionally or alternatively, triggers are presented while the patient is in a staged setting (or a virtual reality setting), to assess the effect of the triggers. Optionally or alternatively, this allows a user to practice at home and/or using relative low cost systems.

In an exemplary embodiment of the invention, the virtual reality display includes a head set and/or goggles which show an image and/or an overlay image to the patient. Optionally, head tracking and/or position tracking is used to adjust the image so it appears realistic (e.g., except for when such misalignment is being tested as a trigger). In another example, the "virtual reality" is provided using fixed screens, for example, facing the patient and/or multiple screens to provide an image in a greater portion of the patient's viewing field, optionally including peripheral vision as well.

Optionally or alternatively, the virtual reality display includes a head-mounted sound system. Alternatively, sound, if any, is provided by speakers located in a room.

In an exemplary embodiment of the invention, assessment of a patient is a multi-factorial risk assessment of falls, optionally including neurological assessment etc. Optionally, the virtual reality testing uses the previous assessments as an input to decide which triggers, situations and/or intensity levels (or other trigger parameters) to use.

In an exemplary embodiment of the invention, after assessment, an intervention program, optionally personalized, is selected, optionally including VR training, and/or other interventions, such as cognitive training and/or strength training. In an exemplary embodiment of the invention, the VR training is selected to match the specific weaknesses of the patient and/or include triggers and/or situations which allow not only for training but also for ongoing monitoring of changes in susceptibility to falling (e.g., including triggers that are assumed too weak to cause falls in that patient, so as to see that patient did not regress; similarly, for "difficult" triggers, to see if susceptibility went down).

It is a particular feature of some embodiments of the invention, that an intensive multi-sensory cueing is used that could affect the impairment features of gait while also addressing cognitive domains in dual tasking conditions. In an exemplary embodiment of the invention, the systems and/or methods described herein can be used to specifically target motor and cognitive dual tasking with a VR system for diagnosing and treatment of elderly fallers.

In an exemplary embodiment of the invention, risk assessment can include using, observational (or machine-measured) gait analysis or methods known in the art for using characterizing fall risk. Though it is noted that, in general, using only such methods (e.g., with a VR system) may be insufficient to quantify what occurs as a subject carries out routine activities of daily living, and self-report will be relied upon. In fact, despite its subjective nature and the known problems about recall, self-report is the standard for quantifying at-home fall frequency. It is also noted that unidimensional assessment often does not reflect performance of daily living where complex, everyday challenges may cause the person to fall.

It is a particular feature of some embodiments of the invention that diagnosis monitoring and/or treatment are carried out emulating and/or simulating situations which reflect daily and/or out-of-the-lab experiences.

In an exemplary embodiment of the invention, the use of a VR or other computer controlled display system allows the use of a single system to assess fall risk and provide the treatment to address this risk.

In an exemplary embodiment of the invention, such an 'all in one' system will have the ability to create environments similar to those found in everyday life which challenge older adults and cause them to fall. The VR will take the clinical assessment from the one-dimensional "safe" and artificial medical exam into a more complex multidimensional and realistic scenario. The provocation of falls and assessment of the properties that cause and increase risk for each person will allow for a more individualized, effective and targeted treatment.

In an exemplary embodiment of the invention, the situations and/or triggers used are matched to a patient. Optionally, such matching is based on self-reporting of a user. Optionally or alternatively, matching is by first trying out a set of situations and/or triggers and querying the patients to their relevance and/or familiarity, while also measuring effect on the patient (e.g., via fall and/or near fall detection and/or by monitoring gait and/or effect on a dual task motor-cognitive task.

In an exemplary embodiment of the invention, matching is based on images provided by the patient or others, for example, of sidewalks, a home, an old age home, a park and/or other locations and/or of activities that the patient participates in. this can be used to build a visually and/or cognitively similar situation to challenge the patient with.

A particular feature of some embodiments of the invention is the use of the method for screening of patients. In an exemplary embodiment of the invention, a screening session is between 30 minutes and one hour where a patient is challenged with various test situations and triggers. In one example, the subject walks on the treadmill and is presented with different walking scenarios (e.g., duration of 4 minutes each, for example between 1 and 10 minutes) which challenge and manipulate different tasks (motor, cognitive, dual task). For example, the person is first asked to walk 4 minutes on the treadmill in his comfortable gait speed to assess his baseline ability and/or normal stride length and/or symmetry of walking. Then the person will walk while observing the VR simulation in which obstacles will be presented. This task can be challenging with vertical obstacles of 30 cm and horizontal obstacles of 1 meter. Such a task may require the participant to negotiate the obstacles without contacting them. The frequency of appearance of the obstacles can be, for example, gradual and random e.g., they will first appear every 5 strides (6 meters) for 30 seconds, then advance to 3 steps (3 meters) and then to 8 m. The system can measure the performance as a function of the difficulty level. If the person is able to navigate well at a certain level, then the difficulty level may be increase and the lowest challenging level may be waived. Optionally, in total, 5 trials of 4 minutes each are used. Each trial focuses on a different aspect relating to fall risk (motor, environmental, cognitive etc). The trial in which the most problems have been identified may be repeated twice or more (e.g., with different levels of difficulty to more closely assess the underlying mechanism of falls in this person. Depending on the results, a patient may be sent for more complete evaluation and/or given advice.

In some embodiments, a testing may be provided at home, for example, using a computer display and a home treadmill.

An aspect of some embodiments of the invention relates to testing and/or treating patients by provoking the patients with situations and/or triggers designed and/or selected to cause falls, near falls, degradation of gait and/or other cognitive and/or motor and/or functional effects.

In an exemplary embodiment of the invention, a system for such a use includes a display and a controller programmed to provide, using the display, one or more situations and/or triggers. In an exemplary embodiment of the invention, the controller, for example, a computer, is programmed with situations and/or triggers matching to a diagnostic, monitoring and/or treatment plan of the patient. Optionally or alternatively, standardized tests are stored thereon as well. Optionally or alternatively, standardized scenarios are stored thereon.

In an exemplary embodiment of the invention, the display is a VR display (e.g., a screen, wall projection or goggles). Optionally or alternatively, the display is a standing display. Optionally or alternatively, the triggers are audio triggers. In some embodiments, the situation is provided, at least in part by a room and its decoration. Optionally, the system (e.g., possibly other than the display) are not coupled to the patient, so the patient is unencumbered by wires. For example, the display and/or any sensors may be wireless. Optionally or alternatively, the controller is also worn by the patient.

In an exemplary embodiment of the invention, the system includes a treadmill (or other platform) for the patient to walk on. In other embodiments, the patient walks on a floor.

In an exemplary embodiment of the invention, the system can be used to simultaneously present a situation and/or triggers and also provide a dual cognitive task. Optionally, the system includes inputs from the user (e.g., voice, buttons, touch screen) and/or measurements (e.g., of gait, falls and/or near falls, for example, using pressure sensors and/or accelerometers and/or video cameras and/or position sensors) to assess an effect of the situation and/or trigger.

In an exemplary embodiment of the invention, the system is configured for remote operation and/or processing of collected data, for example, allowing a system to be placed in an old age home, but operated and/or monitored by remote.

An aspect of some embodiments of the invention relates to determining a fall or near fall or gait problem by activity in the frontal lobes, for example, based on changes of blood flow thereto. In an exemplary embodiment of the invention, when such flow is reduced, it is assumed that the cause of the problem is motor and blood is being diverted to motor areas. If such flow is increased, it is assumed that the cause of the problem is cognitive and blood is diverted to the frontal lobes, for example, to improve attention or executive function. In some cases, it is assumed that such changes in blood flow indicate the method being used by the patient to solve the problem. Optionally, training of the patient includes teaching other methods (e.g., motor rather than cognitive or vice versa) and such feedback is used to assess if patient is learning the more useful response. Some embodiments of the invention may be used as an assessment tool to observe the effects of implicit motor learning and the transfer of this learning to functional ability and/or may also be used as a neurofeedback approach by which the FNIRS (Functional Near Infra Red Spectroscopy) device is worn on the forehead of the person while he is training with the VR system. The continued measure of blood flow to the frontal lobe could be coupled to a feedback mechanism that will provide information on correct or incorrect motor strategies.

In an exemplary embodiment of the invention, a fall or near fall could be detected based on the increase of blood flow, optionally in conjunction with other physiological measures, such as heart rate and acceleration of a limb. In some embodiments, frontal blood flow assessment is for clinical use only whereas ECG and/or galvanic skin conductance (used as an indication of psychological or physiological arousal and a measure of the sympathetic nervous system) could be measured continuously also during daily life with the ambulatory device.

An aspect of some embodiments of the invention relates to treating a gait disorder and/or reducing a risk of falling by training with fall-causing provocations and, optionally, implicitly teaching strategies of movement that will be efficacious in negotiating these provocations. In an exemplary embodiment of the invention, such training is used in conjunction with teaching of alternative strategies, cognitive and/or motor and/or mechanical to use in situations where fall risk is increased and/or if a patient receives an indication that fall risk is increasing. Such an indication is optionally provided by a worn device that provides biofeedback when the gait pattern is not correct or is identified as at a risk for falls. This training also allows for implicit motor learning opportunities due to the feedback provided on knowledge of performance. This feedback may be personalized for the person's needs and can optionally allow for a graded progression in difficulty level. In some embodiments, a worn or implanted device is used without VR, for example, including a sensor and a stimulator, for example, being implemented in a smartphone.

An aspect of some embodiments of the invention relates to screening of patients for fall risk. A potential benefit of some embodiments of the invention is that within 20 minutes (e.g., 5 trials of 4 minute walks each), one can not only assess and diagnose fall risk, but also understand the nature of the individuals' problems and/or possibly prescribe and/or tailor the most appropriate personalized care that will address the person's needs. As an example, an older adult could be evaluated by the system in a clinic as a result his physician can recommend physical therapy to address issues of foot clearance that increases this person's risk for falls. After receiving therapy, the client will come back to the clinic for another evaluation by the system to assess the efficacy of the intervention and the current risk for falls. If there was improvement, the clinician can recommend lifestyle modifications such as continued physical activity etc. If there has been no change or even a deterioration then the clinician can prescribe an intensive intervention via the system described herein. Some complimentary parts of some embodiments of the invention enable the use of its components as a screening tool, evaluation and assessment tool and finally as a training device. Optionally, screening is repeated periodically, for example, on a tri-monthly, yearly or bi-yearly basis and/or in response to functional changes and/or neurological events in the subject.

In an exemplary embodiment of the invention, partial screening is provided by worn accelerometers or other motion sensors which may identify a problematic gait. Optionally, such a worn device can provide warning (e.g., pre-fall or near fall) and/or generate an alarm or communicate with a center to call a subject in for testing, if a change in risk is detected. Optionally, in-depth diagnosis and/or evaluation are provided using a VR system, for example, at home or at a clinic. Optionally or alternatively, a worn device will also include a cuing system to remind a subject to correct his gait and/or enter a defensive mode.

In an exemplary usage, Using the information provided by the system, after a baseline assessment, the system can automatically (or a human, manually) create individually-tailored training programs to train the motor system of the subject to adapt for strategies that distance them from the physiological circumstances that lead to falls. This may empower the provision of quality care, individualized to the person's needs. For example, if the evaluation highlights that a subject has mainly problems with gait asymmetry, the focus of the treatment will be on motor learning that will result in modifying the gait pattern to become more coordinated. If the system concludes that the person's risk of falls is high because of cognitive problems and impaired divided attention then the system can recommend to use the VR simulation to provide training that is rich with cognitive stimulus tasks such as visual spatial processing, attention, planning and executive function. In another example, if the person has difficulties in step clearance and obstacle negotiation then the training will focus on provided different obstacles and teaching the participant strategies of movement. Results shown below suggest that training with such a system can improve gait, dual tasking and/or cognitive abilities, and/or lower the risk of falls.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Adaptive System and Methods

In an exemplary embodiment of the invention, a "smart" adaptive system is provided, which allows for the provocation of falls in order to assess the risk of an individual and/or optionally uses this detection capability to provide an individualized treatment paradigm, optionally specifically designed to address each person's needs, which may lower the risk of falls and/or maintain health to the extent possible.

In an exemplary embodiment of the invention, such an 'all in one' system will comprise of a treadmill and a virtual reality (VR) simulation.

FIG. 1 is a schematic showing of such a system 100, in accordance with an exemplary embodiment of the invention.

A subject (patient) 102 will walk on a treadmill 104 while immersing in a VR environment 108 (or possibly a non-immersive display screen). In an exemplary embodiment of the invention, the subjects will wear a safety harness 110 to prevent injury but one that does not interfere with their mobility. Optionally, wearable sensors (or camera readable markers or other types of fiduciary marks) 106 will be attached to specific body segments on the person and allow for a closed loop system to detect the movement and reaction to the VR scene and/or to serve as direct input to the VR scene. The use of a closed loop system (e.g., acquisition—processing—actuation and again acquisition . . . ) optionally reduces the need for continuous assistance by clinicians.

In an exemplary embodiment of the invention, the cameras (e.g., or others, such as "Kinect"-type motion, gesture and posture capture cameras) are used to also collect posture information. Optionally, gait abnormalities are detected and/or predicted based on such posture information and/or on a combination of posture information and acceleration data or other physiological measurements. Optionally, training uses posture information as a feedback to indicate if a patient has learned the desired coping and/or avoiding strategies.

As shown, a user can be challenged, for example, with cognitive tasks and/or motor tasks. Examples of cognitive challenges include, but are not limited to, dual tasking, planning and/or scanning. Examples of motor challenges include, but are not limited to, instructions to or obstacles that require variations in gait speed step height and/or step length. Exemplary scenarios shown include obstacle negotiation, regular walking, endurance walking and/or training.

In an exemplary embodiment of the invention, the system architecture includes smart wearable nodes (e.g., sensors 106) consisting of body sensors (e.g. accelerometers, gyroscopes, heart rate monitors, brain monitors), actuators (e.g., audio and/or vibrotactile), and/or microcontrollers (e.g. 8 to 32 bit), that will act as the interface of the system. Optionally, wireless communication modules (e.g. Bluetooth (BT) or Zigbee or longer range, such as WiFi or cellular protocols). Built in power supplies (e.g., batteries) may be provided. Optionally, the units serve as the gateway to the VR simulation. These can enable a multi-functional personalized system with multi-modal feedback and sensing.

In an exemplary embodiment of the invention, data from the sensors will be transferred (via wireless communication) to the computer simulation and projected to the subject. Optionally, the subject will be shown, instead of or in addition to a first person display, a display on which their movement and performance can be seen through a virtual avatar representing them.

In an exemplary embodiment of the invention, VR simulation includes a graphical design which engages the patients and yet is not perceptually over loading or too complex to hinder understanding of the targeted practice. In an exemplary embodiment of the invention, the design of the system takes into consideration the target population and the potential visual and perceptual changes occurring with age such as diminished depth perception, impaired peripheral vision and a decrease in color definition. The VR simulation is projected on a large screen and is designed to be viewed in 2D. The decision is based on a pilot study that was performed using 3D stereoscopic view, which could be used in an alternative embodiment of the invention. Elderly adults reported that the immersive environment caused dizziness and was to overwhelming overtime. The 2D application increases the sense of presence but without the potential hazards of cyber sickness. The VR simulation may be matched to the patient's abilities. Optionally, more realistic (though optionally less tasking) situations are used in patients with more limited ability. In an exemplary embodiment of the invention, the VR simulation will encompass one or more of obstacle negotiation and cognitive tasks that include tasks of executive function such as decision making, memory, planning, response selection, response inhibition, divided attention and sustained attention. Optionally, one or more tasks are provided in addition to portrayal of a scene, for example, a mathematical or a listening task.

In an exemplary embodiment of the invention, the system will provide scenario's that often induce falls in the elderly in everyday life such as negotiating obstacles while avoiding distracters and attending to a temporal constraint (e.g., similar to trying to catch a bus). If the person is able to successfully attend to the task without falling, the system will automatically provide a more challenging task. If a fall is provoked a different scenario will be provided to address other difficulties that can cause falls in order to fully assess the person's risk. These could include walking under visually obstructed conditions, crossing narrow pathways, stressful situations, scenario's that require quick decision making and so forth.

In an exemplary embodiment of the invention, the tasks and/or scenarios are personalized. Specific tasks could include for example a simulation of a kitchen, in which the person is required to reach forward and grab ingredients for a cake from the cupboard. The simulation embodies a motor task, requiring balance, functional reach and center of mass displacement as well as cognitive tasks that relate to scanning the cupboard and remembering the list of ingredients needed. Another example could be the use of a simulation of a board walk on which different types of obstacles are placed. Here the motor task is intuitive and requires stepping, single limb support, balance, clearance of the foot over the obstacle, and the cognitive tasks include planning of the actions required (when to lift the foot to pass over the obstacle), perception and attention. Subsets of the tasks, in which fewer sub-tasks are required, may also be used. Selection of tasks depends, for example, on the person's needs and the specific weakness or impairments to provide the most appropriate personalized treatment. For example for a person who has low clearance and is likely to trip and fall because he is unable to lift his feet up high, an obstacle course may be prescribed.

Figure 2:
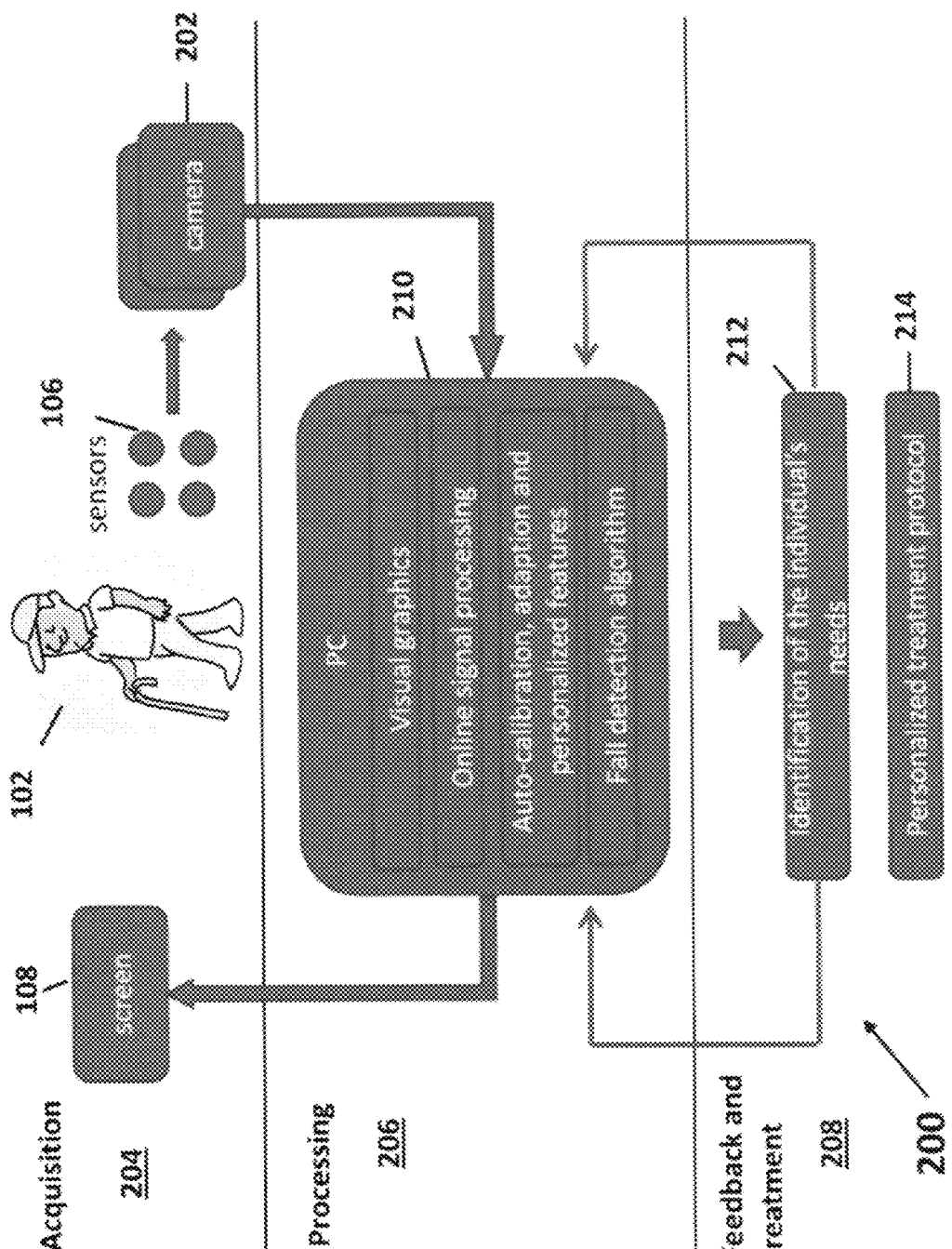
FIG. 2 is a schematic block diagram of a VR-based system in accordance with some exemplary embodiments of the invention.

FIG. 2 is a schematic showing of a system 200, in accordance with an exemplary embodiment of the invention. As shown, system 200 has three conceptual parts, acquisition 204, processing 206 and feedback 208. Some parts of the system, such a display or a processing system may be located remotely from the other parts. Optionally, reports on a patient test and/or changes therein may be automatically and/or electronically sent to a caregiver and/or a monitoring professional, such as a physician. In an alternative, a remote view may connect to the system and initiate data collection, for example, to enable a tele-medicine approach in which a clinician can view the person's performance in real time.

At acquisition 204, a display 108 is used for one or more of creating challenges, creating a cognitive load, engage and/or sustain a subject and/or provide feedback to the subject. In an exemplary embodiment of the invention, sensors and/or a camera 202 are used to collect information about patient 102.

At processing 206, a processor, for example, a PC or an embedded wearable processor provide one or more of generating visualizations, on-line signal processing, fall detection and/or adaptations, such as auto-calibration, adaptation and personalization features. In an exemplary embodiment of the invention, data collected from the sensors is run through a detection algorithm that identifies high frequencies in the gait pattern suggesting an over powered walking pattern (which is common during missteps and falls). Optionally, information provided by the VR (e.g., one or more of the number of obstacles successfully passed, which obstacles, distance of the forefoot from the obstacle when first passing it, the distance of the heel of the advancing foot from the obstacle upon initial contact with the ground; i.e., heel stroke) is used to adapt the obstacles continuously and/or change the difficult level based on the person's performance system to provide a more guided evaluation and training.

At feedback 208, identification of patient needs 212 is optionally provided and optionally used to vary the processing. Optionally, a personalized treatment protocol 214 is generated.

In an exemplary embodiment of the invention, the system will be adaptive and have a "learning" paradigm in which if a person encounters difficulty with one of the scenario's, the system will introduce a similar simulation but with a higher level of difficulty and/or a different task and/or task type (or situation) to tease out the parameters that increase the risk of falls for this particular individual. Optionally, a set of tasks and their relationship for selection for testing is provided ahead of time. Alternatively, it may be manually selected. At least in this sense the system may personalize the risk for each individual. Optionally, using a mathematical algorithm, the system will provide a composite score of the person's risk of falls. This may include for example one or more of: the conditions he is likely to fall in and the most impaired properties (cognitive or motor) that will cause this person to fall. This form of detection may provide a useful individualized and/or accurate assessment of the person's needs and this composite score will allow the clinician to assess fall risk and then prescribe the most efficient care.

As noted, a worn (e.g., on belt, necklace or wrist) device may be used, for example, to collect data, to generate alerts and/or provide feedback to the patient and/or others. In one example, such a device includes one or more movement sensor, such as accelerometers and/or one or more cerebral activity sensors. The device and/or a paired device processes collected data and generates an alert, generates a signal to the patient (e.g., cuing) and/or communicates with a remote server. For example, such a device may provide an indication of high risk if the patient's gait changes suddenly, starts to change slowly (e.g., as patient gets drunk) or as a detector when a fall actually occurs.

Figure 3:
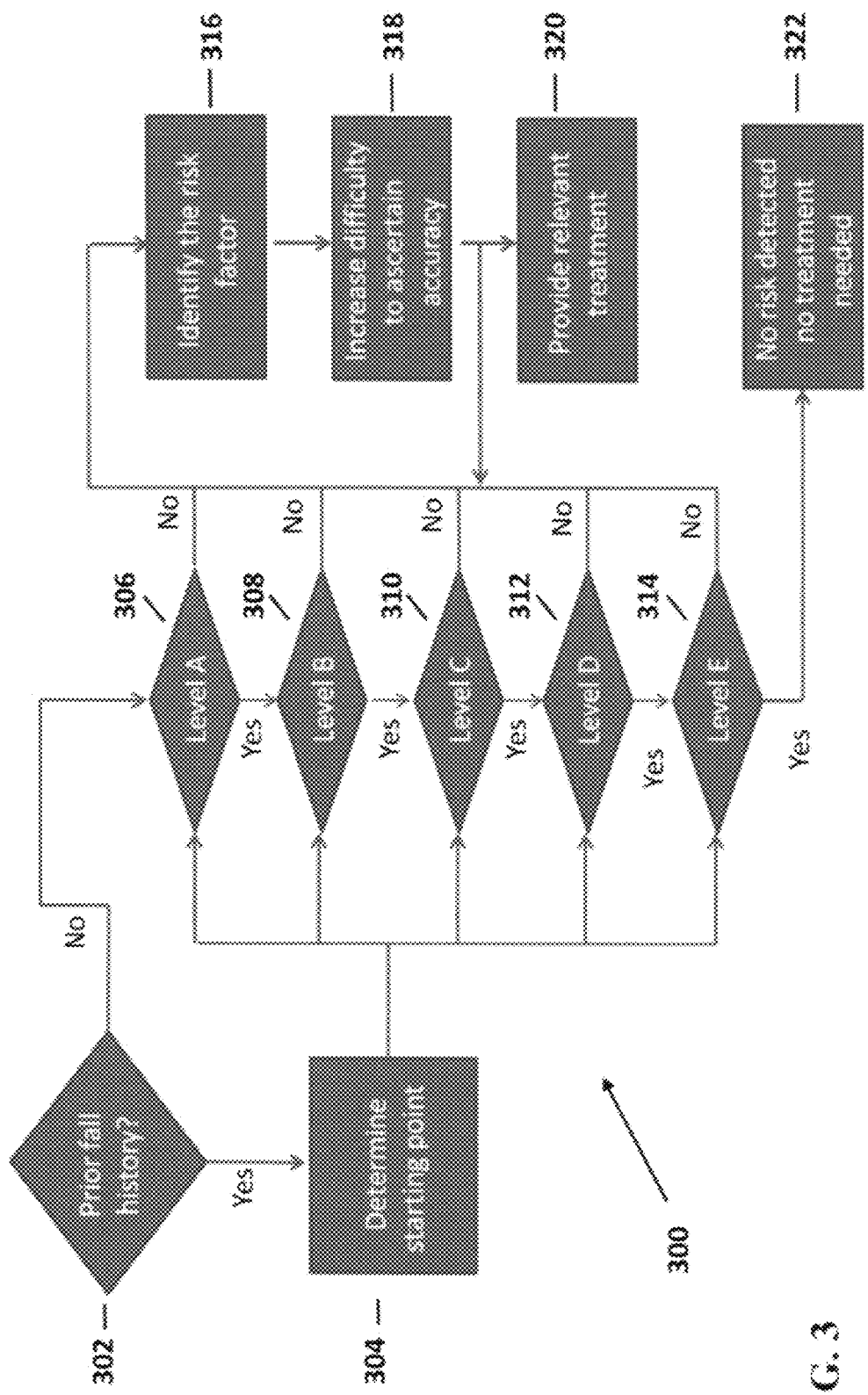
FIG. 3 is a flowchart showing an exemplary gait and/or fall assessment method in accordance with an exemplary embodiment of the invention.

FIG. 3 is a flowchart of an exemplary such method of fall assessment, in accordance with an exemplary embodiment of the invention.

At 302, prior fall history is assessed. If none, the method may be used for screening, and starts at a lowest level, 306.

If there is prior fall history, a starting point may be manually or automatically determined, for example, based on that history.

Levels A-E (306-314) may be tried out, for example, in series, in a different order and/or interleaved.

If all levels are passed (e.g., relative to some threshold), it may be determined that no risk is detected 322 and no treatment needed (or some preventive treatment may be provided).

At 316, if a subject fails at some level, a risk factor may be identified or narrowed down based on that failure and/or based on performance in other tests (e.g., motor and/or cognitive).

At 318, the difficulty may be increased and/or other parameters changed, for example in order to increase accuracy of diagnosis.

At 320, based on the diagnosis, one or more relevant treatments may be suggested. For example if the system concludes that the person's risk of falls is high because of cognitive problems and impaired divided attention then the system may prescribe training that is rich with cognitive stimulus tasks such as visual spatial processing, attention, planning and executive function. In another example, if the person has difficulties in step clearance and obstacle negotiation then the training may focus on provided different obstacles and teaching the participant strategies of movement. The system could also identify the particular risk and the recommendations could be provided to a clinician who can potentially prescribe alternative treatments such as physical therapy exercises, balance training or general conditioning group training.

The levels (A-E) optionally refer to different difficulty levels and the involvement of the cognitive and motor constraints. For example: level A could include a simulation with low level obstacles both horizontal and vertical with no distracters, level B could include higher level obstacles and the addition of narrow pathways. In level C passages will be introduced, these could include doors, bridges and tunnels, level D will include distracters (auditory, visual) and level E could include combined dual task activities, higher level obstacles, narrow pathways, passages, and distracters. Different numbers and/or contents of levels can be provided. Also, an increase in difficulty can be using a continuous variable (e.g., delay between start and end of task) optionally being varied based on previous results. Changing between levels may be used, for example, to bracket a patient's ability with both low scoring levels and high scoring levels.

Optionally, the system (or a different, optionally compatible, system) is used to provide training based on the assessment. In this regard, VR training can be a link between motor and cognitive training and/or a means of significantly enhancing the clinical utility of the "motor" training while performing cognitive tasks that require attention and decision making.

In an exemplary embodiment of the invention, task specific and appropriate training can be provided using a VR platform for older adults. This form of training allows for a varied, meaningful and/or purposeful context that matches the individual's needs and increases patient empowerment, while, optionally, maintaining interest (e.g., using interesting visual scenes as background). Optionally or alternatively, treatment can be graded in terms of both physical and cognitive challenges. For example, the system can use the multisensory feedback provided by the VR to augment training and/or drive neuroplasticity pathways. Auditory and visual feedback may be automatically given by the VR simulation in the form of knowledge of performance (KP) if errors occurred (e.g., stepping on an obstacle) and/or knowledge of results (KR) e.g., in the form of total time walked and total number of obstacles safely avoided (similar to a score in a game) and success/failure ratio. In addition, for some avatar designs (if an avatar is used), the person can see the pattern of movement he performs by looking at the virtual avatar. The avatar can represent the specific movements of the person and hence for example if the person is walking with an asymmetrical gait by which the left leg takes a longer step than the right, this would appear on the screen (and is optionally marked) and the person will have real-time feedback which will enable him to correct and regulate his steps. Similarly, if a person is walking with short steps or with a wide base of support, this will be projected, and as a result could elicit a behavioral change. Such feedback is known to assist in generalized learning by providing participants the reference as to how to correct the next attempt by self-assessment and problem solving. This feedback is thought to allow for the development of new motor programs, transfer, and retention of training effects, creating a behavioral change that has resounding effects on physical activity, functional independence and fall risk, but has apparently hereinto been unavailable for this type of need. Indeed, as a result of motor learning and the behavioral changes, benefits, when implementing some embodiments of the invention, are expected to persist long after the training period, for example, several days, weeks and/or months after a training session and/or a series of training sessions (e.g., 1-18 sessions). In a pilot study that was conducted by the inventors, training effect of 6 weeks of intervention with the system on a treadmill, were sustained for 6 months in 5 healthy elderly women with a high risk of falls, even off a treadmill. It is expected that due to the implicit motor learning and hence plastic brain changes, training effect will transfer to everyday life activities and will have a sustained behavioral and functional effect.

In an exemplary embodiment of the invention, gait assessment is done using accelerometers and gyroscopes to assess spatial temporal parameters of gait (e.g., gait velocity and stride time) as well as measures of consistency (i.e., gait variability and gait regularity). Optionally, in healthy older individuals, it is expected to observe gait speed in a range between 0.8 m/s-1.4 m/s with a mean stride average of 1.2 sec and gait variability of approximately 2%. These parameters will change dramatically in individuals with high risk of falls (e.g., slower gait speed and gait variability of as much as 5% or more). Under challenging conditions, like those imposed in the VR system, these parameters will also change (eg. increased variability). The degree to which they change reflect, in part, the subject's ability to compensate and preserve a normal gait pattern in the face of "extreme conditions", such as those that occur during complex, everyday walking.

As noted, not only falls need be assessed. For example, one or more of gait impairments, asymmetry (e.g., as in stroke), orthopedic issues (e.g., even subclinical) dystonia (e.g., episodic gait abnormalities) pre clinical deficits in motor-cognitive performance, ataxia, gait changes secondary to psychological deficits (e.g. ADHD, major depression) and/or others may be detected.

In particular, by challenging the patient with various cognitive, motor, perceptual and/or other loads, rare events can be made more common and/or more intense.

In particular, diagnosis can include measuring an amount of disorder and quantifying a risk, rather than merely relaying on subjective and binary assessments by physicians.

In particular, diagnosis is optionally used to pinpoint the underlying cause (e.g., motor, cognitive, environment, orthopedic, integration, other), so that treatment and/or avoidance can be planned and/or monitored.

Exemplary Usage Scenarios

One important usage scenario of some embodiments of the invention is using a system as described herein to identify older adults at risk of falls and provide an early personalized preventive intervention that will help them maintain a healthy life style and avoid the complications of falls. Such a system is optionally set in every (or many) hospital and/or clinic and used as an assessment tool for clinicians. It can also be used in rehabilitation centers, nursing home facilities and gyms as a training device that will provide challenging, motivating and effective intervention utilizing both motor and cognitive domains, to bring the most effective solution to the problem.

In an exemplary embodiment of the invention, the system is used to identify potential "fallers" prior to the first fall, which usually starts the vicious cycle of falling, withdrawal and more falling. Since current treatment methods are not yet optimal, identification of new effective interventions that reduce the risk of falls is extremely important. Ultimately, a method that would allow predicting who is at risk of falling and provide an effective treatment approach may help to reduce the costs and burden of falls on society and enhance the functional independence of the growing elderly population.

In an exemplary embodiment of the invention, a diagnostic, testing and/or treatment session (they may have different values of the parameters), may be of length, for example, between 3 and 100 minutes, for example, between 10 and 30 minutes. For example, between 1 and 50, for example, between 5 and 20 different provocations may be provided, optionally with some repetition (e.g., an average of between 1.1 and 4 repetitions per scenario). For example, between 1 and 20, for example, between 3 and 15 falls and/or near falls may be collected (or intended to be collected, e.g., by increasing frequency and/or difficulty of challenges and/or varying type) per session.

In an exemplary embodiment of the invention, a risk assessment includes a score, built of, for example, a weighted combination of the number of falls, number of real falls and/or deficient in cognitive performance and/or speed of walking, weighted, for example, by the level at which they occur. Optionally or alternatively, a table is used which translates performance into a score. Optionally, a multi-dimensional score and/or assessment are provided, for example, for different types of triggers and/or cognitive interference situations. As an example for a person with a history of falls that as per self report of the patient occurred because of tripping over things, when challenged with an obstacle navigation task, it is expected that the system will detect approximately 15-20 events with the majority (60-90%) occurring before or due to obstacle crossing. This will be complemented by high gait variability and step irregularity (~3% and ~1.5 prs). All these measures combined added to high risk of falls score.

Exemplary Invented Cases

Mr. Levy is 69 years old, he is retired and is living in his home with his wife. His wife says he is unstable and is afraid he will fall. Mr. Levy thinks she exaggerates and feels fine. He goes to his physician which evaluates him and finds no neurological problem or muscle weakness. In all balance performance based tests, Mr. Levy demonstrates a slight decrease in performance but his score is still within the normative range for his age. The physician decides to send him for evaluation in the fall clinic just to be on the safe side. He is referred to the Gait and Neurodynamics Laboratory where he is evaluated by a system using virtual reality. Mr. Levy is started off with the lowest level of difficulty; obstacles alone. He is able to complete the tasks successfully therefore more challenging constraints are introduced. He is able to negotiate bridges and tunnels and narrow passages without a problem, but when distracters are introduced (e.g., level D) he suddenly slows down and his performance is diminished with a low success rate of maneuvering around the obstacles. The system computes his score as moderate and prescribes a training protocol that includes high level virtual obstacle navigation under challenging conditions of dual task and distractions. Mr. Levy receives training for 8 weeks and declares he feels more confident and able to perform better during everyday activities. The scores concur. Both Mr. and Mrs. Levy are happy.

Mrs. Cohen has had PD for 4 years; she recently started suffering from instability during gait, and even sustained 2 falls in the past year. She reports to her clinician that her first fall occurred while she was walking in the street talking to a friend and the second one when she was on a narrow and uneven side walk. The clinician requests that she be evaluated for fall risk and recommends a training activity. She is referred to the Gait and Neurodynamics Laboratory where she is evaluated by a system using virtual reality. Because of her prior falls history she is put on the system and level B is selected for her evaluation. During the evaluation Mrs. Cohen sustains a misstep on the treadmill while trying to step over a virtual obstacle. Difficulty level is increased to include higher and more frequent obstacles. Mrs. Cohen again fails to negotiate the obstacles safely. Then Mrs. Cohen receives a new simulation consisting of an urban environment filled with distracters, here she is hardly able to navigate and successfully complete the task. The system defines her risk as high and configures a training protocol that includes dual tasking activities in different scenarios. Her training consisted of gait components such as increasing step length and step clearance while engaging in a navigational cognitive task that required her to scan the environment for the obstacles, plan the action required, ignore distracters along the way (response inhibition), maintain attention to the task, which task and/or its complexity being optionally based on her performance. Mrs. Cohen trains for 8 weeks on a daily basis, recording on the system, before each training session starts, a self-confidence score about her motor status and her medication intake. On-site technical assistance was provided when necessary.

Mrs. Jones is a 62 year old woman living in the community. She comes to her physician worried after her best friend sustained a hip fracture secondary to a fall. She requests a physical check up and an osteoporosis exam. The physician sends her for a bone scan which comes out positive for osteoporosis. Her physical exam however reveals no serious problems in balance, gait or physical fitness. She is referred to the Gait and Neurodynamics Laboratory where she is evaluated by a system using virtual reality. She is started off with the lowest level of difficulty; obstacles alone. Mrs. Jones is able to complete the tasks successfully therefore more challenging constraints are introduced. She is able to negotiate bridges and tunnels and narrow passages as well as the combined dual tasking challenge (level E). The system computes her risk score as low and she is sent home with recommendations for safe mobility and fall avoidance, but requires no treatment at this time.

Exemplary Variations

The system proposed herein is optionally designed for the elderly population in mind to address the devastating increase in falls and its consequences. Many pathological conditions however share similar problems as the elderly population both in terms of falls risk, but also in terms of motor and cognitive deficits.

In an exemplary embodiment of the invention, the systems described herein are used also or instead for other pathological conditions than falls. In such uses, the system is optionally programmed to detect the other pathological condition. Optionally or alternatively, the system is programmed with triggers, situations and/or training programs that provoke and/or train for the other pathological conditions. Optionally, a training program for multiple conditions is provided, with some situations adapted for one pathological condition and some for others.

For example, freezing of gait (FOG) may be provoked using, for example, images of narrow passageways, to provoke FOG and/or near FOG conditions and/or to train a subject for them. Optionally, FOG is detected using one or more physiological sensors, for example, an accelerometer, which may also be used for other disease conditions. Additional details re FOG detection and/or treatment may be found in a co-filed PCT Patent Application No. PCT/IB2012/055454 having International Filing Date of Oct. 9, 2012.

For example the system can detect impairments and/or treat people post-stroke or those affected with neurodegenerative disease. Patients with neurological conditions often suffer from balance and mobility impairments. Issues of symmetry could be addressed as well as difficulty to adjust weight shifting and balance reactions. In addition to the motor problems, neurological pathologies are often accompanied by cognitive deficits such as perceptual impairments, decreased executive function, dual tasking ability and frontal inhibition. The integrated system could provide an assessment of the impairments and/or deliver the most appropriate type of intervention which could improve their rehabilitation.

Another example is dystonic gait. This type of gait disorder is very difficult to assess and treat due to the high variability within and between patients. A system like the one described, could possibly provoke and uncover the dystonia even in the subclinical phase and potentially provide the necessary treatment. Extending from this, such an integrated approach can be of significance for children with Cerebral Palsyspinal cord injury and head trauma as well as ataxia both juvenile and traumatic to address their gait pattern, their ability to function and address challenges in everyday life and provide feedback of performance to prescribe appropriate training and treatment. As examples, challenges to be used with patients post stroke could relate to improving symmetry and improving weakness on the hemiplegic side. This could be done by providing high level vertical obstacles to the sound limb to encourage more stance on the hemiplegic limb. For patients with TBI who have difficulties in cognitive function, the system can provide tasks of planning the path of walking, memorizing different objects on the path, and sustaining attention on the task while ambient distracters appear.

Such a system could also be used to improve performance in the healthy population, such as in elite athletes. The system could, for example, assess probability of injury due to deficient gait pattern, subclinical orthopedic weakness that could cause make the athlete more prone to injury, such as subclinical asymmetry and over activation (overuse)) of one extremity. Subsequently the system could provide training to enhance performance, improve weak spots in a more correct kinematic approach and even enhance performance on specific tasks such as hurdle running by teaching new improved strategies of performance.

Exemplary Implementation and Experiments

In this section various practical implementations as a system are described, including results from utilizing these implementations for diagnosing and/or treating people in accordance with some embodiments of the invention. It should be noted that the teachings herein are not limited to the specific system tested.

Exemplary System Architecture

In this exemplary embodiment, the system is designed to integrate both online locomotion stimulating techniques and monitoring technologies. The system automatically identifies the walking patterns of the individual, introduces freezing provoking situations (a kind of 'freezing stress test') in a controlled environment, quantifies and characterizes the freezing episode, and assesses the best repertoire of treatment suitable for the individual.

Figure 4A:
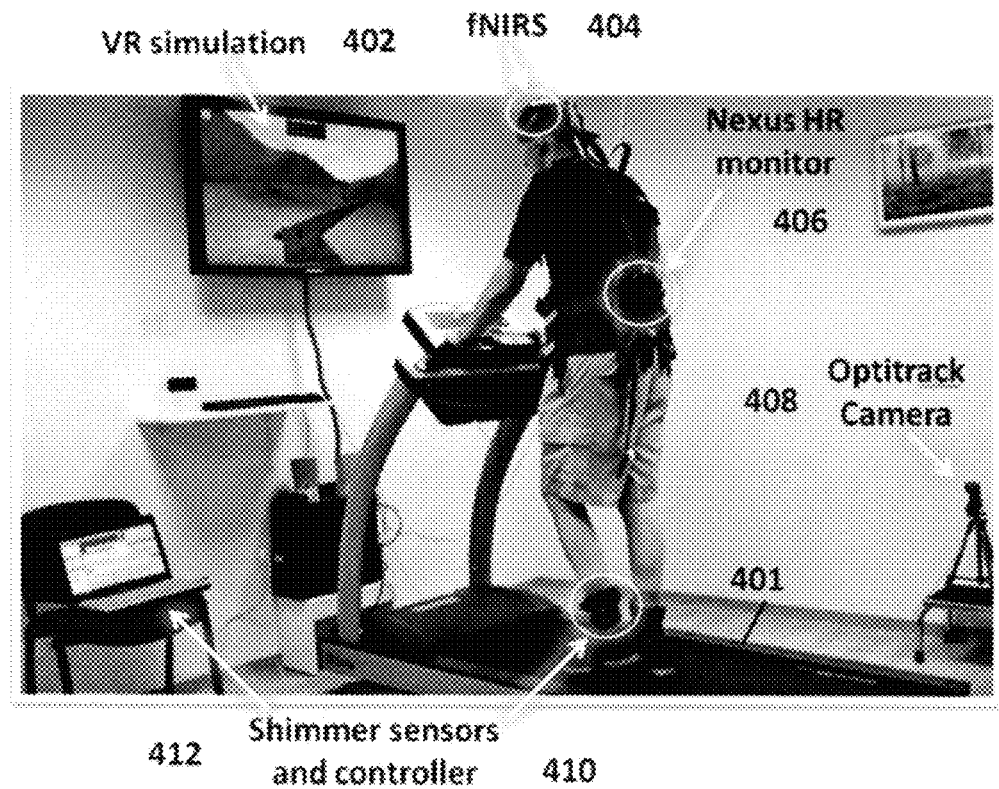
FIG. 4A is an image of a fall assessment system in accordance with an exemplary embodiment of the invention.

FIG. 4A is a picture of such a system. This 'all in one' system is comprised of a treadmill 401, a virtual reality (VR) simulation 402 (here shown on a display, rather than, as an alternative, goggles), and accelerometers 410. The patients walk on treadmill 401 while immersed in the VR environment 402. Small passive markers are optionally attached to the patient's shoes or other parts of the patient's body or clothing, optionally using a harness, and act as the interface or gateway to the VR system (e.g., via a camera 408 or other position and/or orientation tracking system). In an alternative embodiment a marker-less tracking system is used. Using two optitrack cameras 410, the movements of the feet are detected and inserted into the VR simulation using an avatar (e.g., as shoes on the screen) that accurately reflected the movement of the feet in reaction to the VR scene.

Optionally, the patient wears a safety harness. Optionally or alternatively, the patient wear a heart rate monitor 406. Optionally, the subject is wears fNIRS sensors 404 (e.g. covered by a head cap) and/or ECG sensors. These cerebral sensors are optionally used for physiologic monitoring and/or validation purposes. A controller 412 is optionally used to control and/or read sensors 410 and/or provide input to VR environment 402.

In an exemplary embodiment of the invention, EEG or other means are used instead of or in addition to fNIRS to assess changes in cerebral activity. A potential advantage of using both EEG and fNIRS is that EEG has better temporal resolution and fNIRS has better spatial resolution.

In an exemplary embodiment of the invention, EEG can be used to measure brain electrical activity at rest and/or to measure (e.g., after filtering) brain activity during actions such as walking in the whole brain or in specific regions. Optionally, EEG is used to detect minimal changes in brain activity secondary to focal activation and/or depression of neuronal discharge. Based on the observations of decreased blood flow to the frontal lobe during FOG, it is expected that there will be focal frontal slowing or as called in EEG terms, theta or delta activity over the frontal lobe. Abnormal EEG activity can also be characterized by hyper or hypo synchronization of brain electrical activity in a specific area. EEG activity has been shown to be able to detect not just the movement potential but also the preparatory potential that comes before the actual movement is executed, which may support the use of EEG for prediction and detection of an actual event.

In an exemplary embodiment of the invention, continuous scalp EEG monitoring during walking, for example, by the Oxford ambulatory EEG monitoring system, is used to differentiate between normal stepping and FOG or pre-FOG state by change in background EEG activity over the frontal lobe bilaterally. In an exemplary embodiment of the invention, in the 1-3 seconds prior to the FOG itself and/or during the actual freezing episode, slowing of the background activity will be detected by automated frequency analysis system which is already present in the Oxford system. The system will be able to learn (e.g., using machine learning methods as known in the art) the normal locomotion of the subject treated and recognize the FOG as a significant change from the regular background. Similar detection may be applied for falls and/or other gait abnormalities.

In an exemplary embodiment of the invention, EEG measurement is used to specifically detect increase or decrease of activity in frontal lobes and/or motor regions, for example, based on changes in intensity (e.g., at certain frequency bands).

A potential advantage of EEG is its integration into an ambulatory and/or implanted device.

Figure 4B:
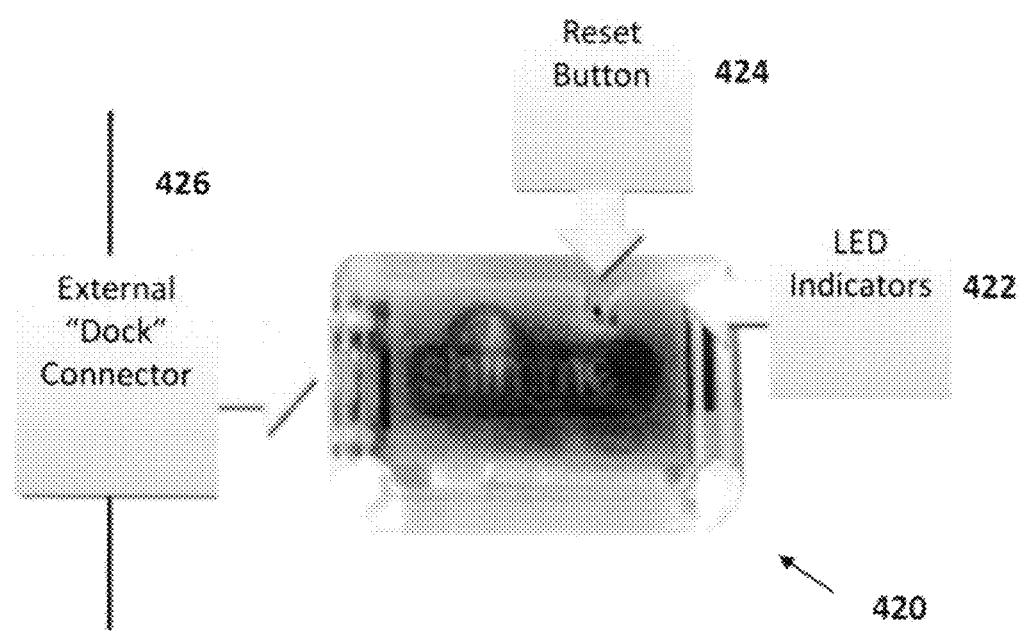
FIG. 4B shows a Shimmer ankle sensor used in accordance with an exemplary embodiment of the invention.

Optionally, acceleration and/or gyroscope sensors, for example, as shown in FIG. 4B are attached to, for example, the ankles of the patient to record the gait patterns of the participants and their reaction to the VR stimulus. Exemplary Shimmer sensors 420 are provided by wwwdotshimmer-researchdotcom. The sensors contain 3-axis accelerometers and 3-axis MEMs Gyro that record data at a sampling rate of 100 Hz via Class 2 Bluetooth Radio, and optionally serve to close the VR simulation loop. The shimmer sensors were use to collect gait measures and the reaction of the participant to the VR scene such as a change in pace or cadence before obstacles, correction patterns and missteps.

Optionally, sensors 420 include an external dock 426, a reset button 424 and/or indicators, such as LED indicators 422. In an exemplary embodiment of the invention, data from the Shimmer sensors is channeled to Matlab software, running on a laptop computer (e.g., 412), that performs real-time synchronization between the 2 shimmers (on both ankles) and runs an algorithm for detecting falls and/or near falls, based on, for example, the fall Index (FI), described below. Optionally, the laptop running the FI algorithm is connected to a computer running the virtual reality simulation using a network cable and TCP protocol. When a fall or near fall is detected, a signal is sent to the virtual reality simulation, enabling the simulation to record the precise location and time of the detected event within the simulation. The system also records the leg on which the event was detected first (the sensor that detected the FOG threshold), the speed at which the patient was walking, the type of trail e.g., the conditions of the VR simulation, the type of obstacles used, if any, and/or the type of FOG provocations provided by the simulation at the time of the event.

Figure 4C:
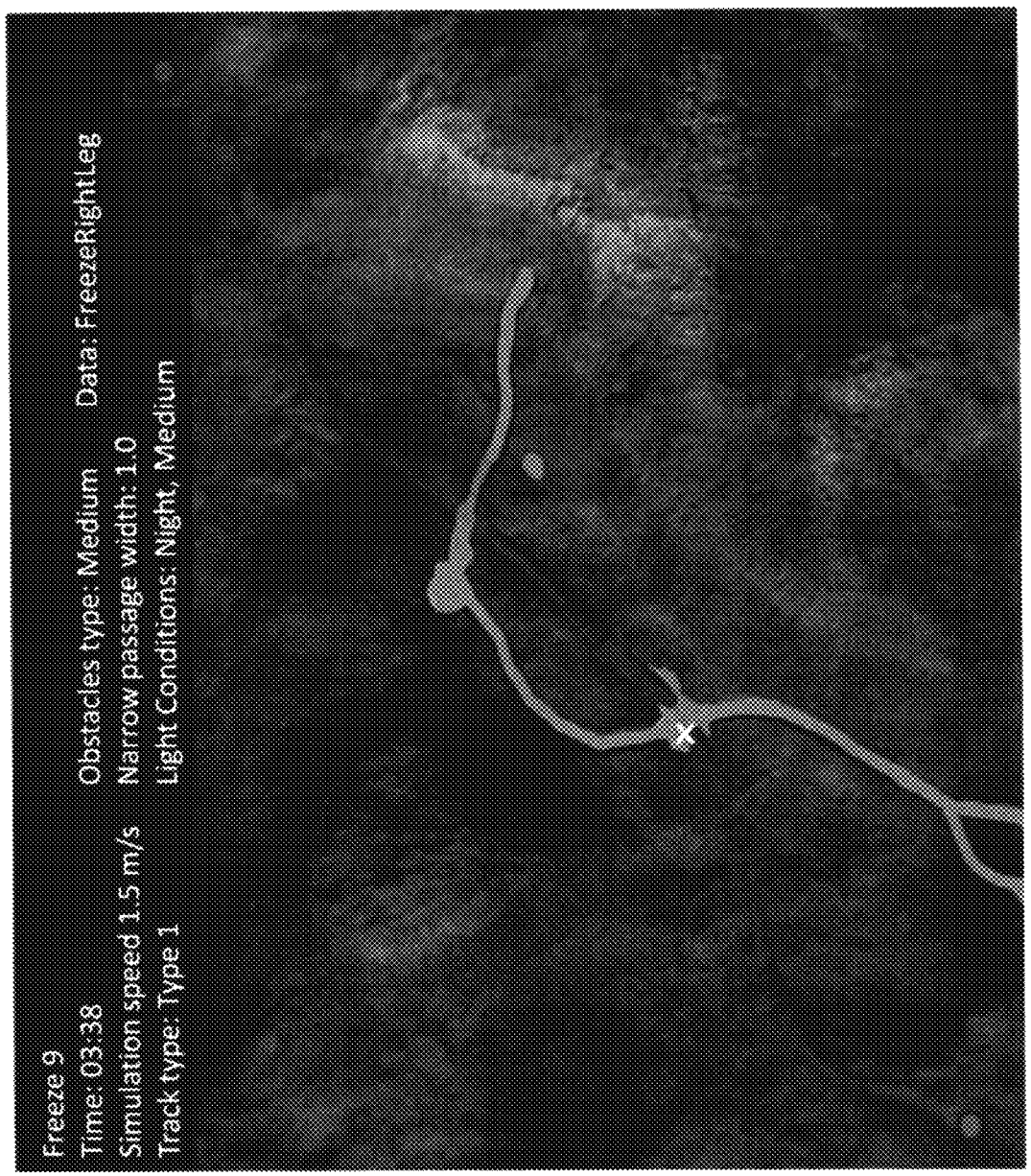
FIG. 4C shows an aerial VR view of a testing scenario in accordance with an exemplary embodiment of the invention.

FIG. 4C shows an aerial visual representation of a VR simulation trail and a recorded fall event within the trail. The time of event within the session is recorded as well as the location on the path (represented by the white x, in this case on the narrow bridge over the virtual river), the type of trail used and the challenges provided (in this case, e.g., day (or night) condition and narrow pathways) and the first leg the event was detected by the shimmer sensors (in this case the right leg). This information could be meaningful as if the pattern occurs always on the same leg, it may suggest asymmetrical use or weakness of one extremity that can be addressed by treatment.

While this implementation may use a dedicated VR simulation, in other embodiments, the VR simulation is part of a commercial game. Optionally, the game is modified to generate a desired rate of challenges, for example, by creating narrowings in pathways. Alternatively, a game is selected with sufficient challenges and the patient simply plays the game, while the system tracks which challenges affected the patient and in what manner.

As noted above, for validation and/or other uses, additional sensors may be used. For example, miniaturized physiological sensors (NeXus MindMedia BV the Netherlands) may be attached to the patient's chest to monitor the patient's heart rate during different scenarios and walking conditions and physical and mental stress. Wireless Functional Near Infrared Spectroscopy sensors (fNIRS-PortaLite, Artinis, The Netherlands) may be placed on the patient's forehead to assess blood oxygenation in the frontal lobe during the test. These signals may reflect frontal lobe activation in response to different stimulations and/or allow the assessment of cognitive function during a fall event and/or other gait challenges. Optionally, these two modalities were used for validation of the fall events. Optionally or alternatively, they can be used as an option in the diagnostic system to provide additional information to the clinician. In an exemplary embodiment of the invention, all systems and sub-systems are synchronized and the sessions were videotaped to allow for further analyses of the fall events.

VR Simulation

Figure 4D:
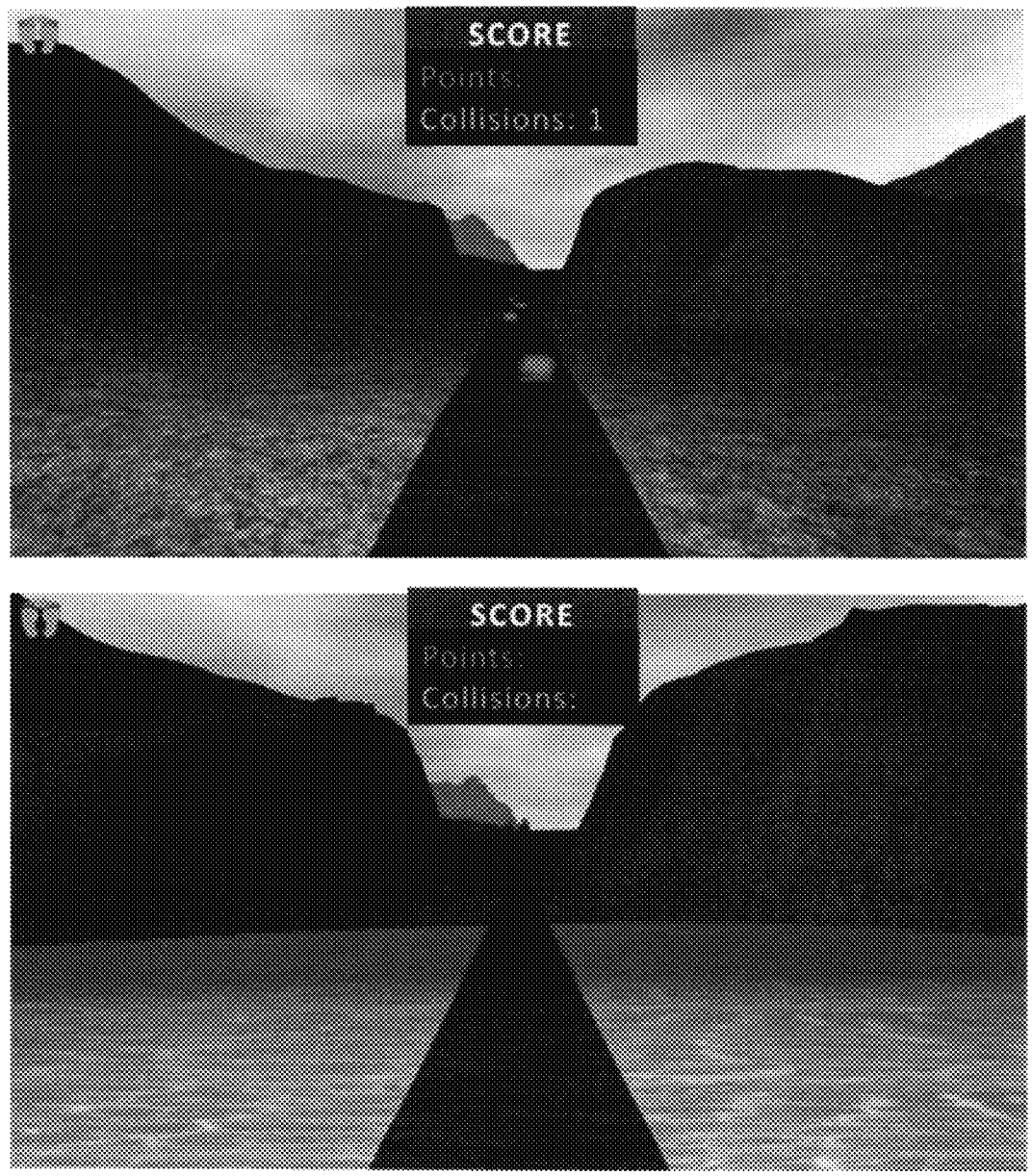
FIG. 4D shows two examples of obstacles as used in accordance with an exemplary embodiment of the invention.

In an exemplary embodiment of the invention, the VR simulation is designed specifically for this use and written in OGRE (Object-Oriented Graphics Rendering Engine) which is a scene-oriented, real-time, flexible 3D rendering engine, programmed in C# using Direct3D and OpenGL as the graphic libraries. The simulation optionally requires processing of multiple stimuli simultaneously. The VR scene consisted of an outdoor boardwalk on which different obstacles were placed. The patients were required to walk on the treadmill while negotiating the obstacles without hitting them. These mobility skills required decisions about step amplitude in two planes (vertical obstacles that required a high step and horizontal obstacles which required long steps) coordinated with walking behavior. See, for example, FIG. 4D which shows two examples of virtual scenes designed to provoke gait problems such as falls. The patient's movement is represented by the shoes on the screen. These provide feedback as to movement, success or failure in negotiating the obstacles and a sense of presence within the VR simulation. A more complete avatar may be used as well. Obstacles presented were either vertical (top represented as a hurdle) requiring high clearance, or horizontal (bottom represented by a black muddy spot) requiring a long step. In order to successfully negotiate the obstacles, patients need to plan the correct response, plan the timing of passage and anticipate the speed required for performance. If successful they receive points on the score board shown on the top of the screen. If an error occurs and the patient touches the obstacle, a red light appears and the attempt is scored as collision. The amount of obstacles changes depending on the difficulty level of the trial and the speed at which they were walking at. The decision as to the side of appearance (right or left leg) is optionally chosen based on the more impaired side, e.g., based on PD (Parkinson's Disease) symptoms (e.g., with 75% of the obstacles presented to the more affected side).

Figure 5:
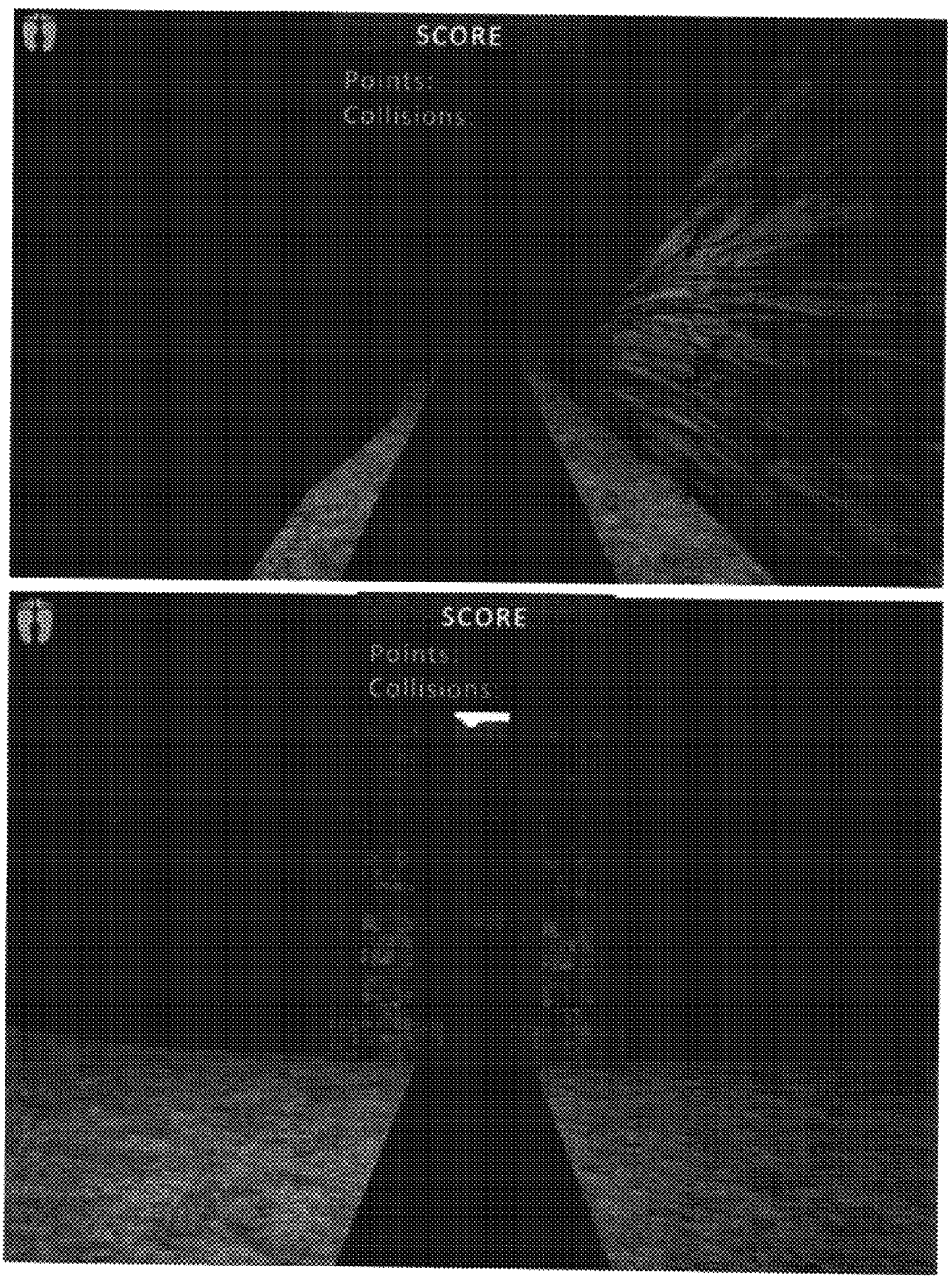
FIG. 5 shows two examples of challenging scenarios, in accordance with exemplary embodiments of the invention.

These decisions are optionally made more difficult using distracters such as changes in lighting and moving objects in the simulation and/or by adjustment of the frequency and/or size of the virtual obstacles. This allows varying the cognitive load independently of the gait complexity and/or potential fall triggers. Optionally, the scene includes gait challenging features such as bridges over rivers, narrow passages, tunnels, a cave, distracters and/or lighting effects. FIG. 5 shows two examples of virtual challenging scenarios. These provocations included features such as bridges over rivers (see also FIG. 4D), tunnels (top) or a cave, narrow passages (bottom) distracters and/or lighting effects, diminishing the visual field or obstructing the view to make planning a higher performance in the obstacle course more challenging and/or perhaps to elicit fear of falling and a more cautious gait, reflecting situations that could occur in everyday life. In an exemplary embodiment of the invention, such features are manipulated with respect to, for example, one or more of their frequency of appearance, size and/or location according to the individual patient's need and/or the difficulty level desired for a trial. In general, these features may be used to introduce challenging situations that may cause an illusion of instability and fear of falling.

In an exemplary embodiment of the invention, the environment imposes a cognitive load requiring attention, planning and response selection as well as processing of rich visual stimuli involving several perceptual processes that have been associated with falls. The VR provides visual and/or auditory feedback upon success or error of crossing the obstacles and/or if a fall/misstep occurs; this feedback is optionally used as part of the therapeutic option. The system optionally provides information as to the location of the fall, the timing of it, the leg on which it was first detected, and/or the duration of the event.

In an exemplary embodiment of the invention, if the system detects gait patterns that are known to increase risk of falls (e.g., missteps, shuffling), a visual and auditory feedback may be provided on screen and the location, timing, the leg on which it was first detected, and the duration of the event may be recorded.

Data Processing and Extraction

As noted the system as described herein is optionally used for one or more of 1) assessing the possibility of identifying individuals with risk of falls using the system, 2) validating the fall risk algorithms against physiological measures, and/or 3) quantifying the risk for falls by different parameters of performance. Below is a description of exemplary methods used for data processing usable for these aims.

Gait Data

Gait data is optionally extracted from the accelerometers in the shimmer sensors. Average gait speed and stride time are optionally evaluated for walking trials. Data collected by the accelerometer are also optionally used to assess measures of rhythmicity and/or stability known to be impaired in patients known to be fallers and those with increased risk of falls. These included, for example, one or more of measures of variability, consistency and symmetry.

Spectral analysis of the calibrated acceleration signal in the locomotion band (0.5-3.0 Hz) is optionally used to assess measures of variability of the signals during gait on the treadmill without obstacles. The peak amplitude the width and the slope of the dominant frequency in the anterior-posterior direction are extracted from the raw signal; a sharper and narrower peak may reflect a more consistent, rhythmic, and healthier gait pattern, e.g., reduced gait variability and/or lower stride-to-stride fluctuations.

A symmetry ratio is optionally calculated based on the difference between acceleration of the right and left sensors during the no obstacle condition.

A Phase Coordination Index (PCI) is optionally calculated from the acceleration signal by determining the stride duration of one foot in the gait cycle (defined as) 360°, where the relative timing of the contra-lateral heel-strikes defined the phase which is represented by $\varphi$ (ideally, $\varphi=180$ for every step). The sum of the coefficient of variation and the mean absolute difference between cp and 180° is defined as the PCI, representing variability and inaccuracy, respectively.

Gait Abnormalities and Misstep Detection

In an exemplary embodiment of the invention, a Fall Index (FI) is calculated from spectral considerations. Wavelets and signal processing are optionally used by identifying specific patterns in the acceleration signal that correspond with high frequency and increased power and regarded as an indication of a misstep. In an exemplary embodiment of the invention, the FI reflects a ratio between the power in gait frequencies (e.g., 0.5-3.0 Hz) and the high gait frequencies (3-8 Hz). In an exemplary embodiment of the invention, calculation of these two measures is performed continuously and/or for each leg separately. In an exemplary embodiment of the invention, a real-time running window is applied to the data from the vertical axis (perpendicular axis to the ground). The size of the chosen window is optionally 1.2 seconds, as an example of a tradeoff between better frequency analysis and minimal latency but a wider range of windows (smaller e.g., 0.6 seconds or less or wider e.g., 1.5 sec or more) may also be used. The information from each window is transformed using, a spectral transform, such as Fast Fourier Transform (FFT) and the distribution of the signal, in the frequency domain, is calculated.

In an exemplary embodiment of the invention, a low value (e.g., compared to a peer group) reflects a strong gait while high values suggest a disturbed or pathological gait. When a change in gait pattern is detected, a signal is optionally sent to the virtual reality simulation. The precise location and time of the occurred event within the simulation, the leg on which the event was detected first, the speed at which the participant was walking in, the type of trail and/or obstacles and provocation provided by the simulation at the time of event are optionally recorded by the VR simulation. The data is then optionally extracted from both the sensors and the VR simulation for further analysis.

Cascade Method to Detect Falls and Near Falls

In this method, a first method (e.g., SFA) is applied on the windows and then a second method (e.g., WWA) is applied on the windows not identified. Preliminary results suggest a hit rate of 85.7% and a specificity of 96.8%. Alternatively, the WWA and SFA methods may be separately applied or other methods may be combined with them. A brief description of the WWA method and the SFA method, in accordance with exemplary embodiments of the invention, follows.

Window-Wise Analysis (WWA)

Description

An optional preliminary stage to running the misstep detection algorithm, is extraction of gait segments, since missteps by definition can only occur while walking. Good gait detection can substantially reduce false alarms generated by noise. While manual annotations may be used to locate gait segments, an automated Gait Detection (GD) algorithm may be used.

Exemplary Gait Detection

Acceleration signal from the lower back has a repeatable pattern in frequencies between 0.5-3 Hz for normal walk. The signal is noisy due to various reasons such as tremor of the patient, different types of walk and placement of the sensor. In an exemplary embodiment of the invention, to minimize false detection of gait, the signal is filtered.

Next, a running window of (for example) 5 sec in length is applied on the vertical and anterior-posterior acceleration signal. The data at each window is convolved with one cycle of (for example) 2 Hz sinusoidal signal that represents a cycle of gait in the filtered data. The resultant signal enables detection of gait by searching for local maxima which represents one gait cycle. Only windows at which 2-15 steps are detected are considered as walking. This range was chosen since gait typically exists in the range of 0.5-3 Hz where 0.5 Hz means a step each two seconds and 3 Hz means 3 steps a second. A 5 seconds window therefore contains 2-15 gait cycles.

Misstep Detection

The data that contains gait is divided into 5 seconds windows. The sensor placed on the subjects may sometimes be tilted or shift slightly during the trials. In order to remove artifacts caused by such movement, a normalization process is optionally applied to each window, subtracting its mean.

In an exemplary embodiment of the invention, the method identifies irregularities in the gait in each window which may suggest a misstep. The procedure is optionally performed both on the vertical (V) and anterior-posterior (AP) acceleration axes. Each window is divided into three segments. For the vertical axis, the maximum in each segment is calculated, resulting in 3 maxima values. If the highest maximum is greater than 1.5 times the second largest of these maxima then the window is classified as suspected misstep (SM). Otherwise the window probably describes normal gait for which the difference between the 3 maxima is expected to be small.

A similar process is optionally performed on the anterior-posterior (AP) axis with two differences. The first is that the minimum is calculated at each segment and the second is that the distance between the lowest minima and 1.5 times the highest minima is checked.

At the end of this stage, a union between the two decisions is performed, meaning that at least one of the decisions on the AP or vertical (V) should be SM in order to declare it as SM, Otherwise it is declared as non-misstep and will not be further examined.

In order to determine that the irregularity happens only in the 5 seconds window and it is not a change in gait due to obstacle negotiation, or start or end of gait, a wider environment around the window is optionally examined. This environment can be an extension of the window by half a window width in each side. In this step it is checked that the maximum of V acceleration, V, Y and Z gyros, and the minimum of ML and AP acceleration, computed in the extended window, occur within the original window, and not in the extensions. Extrema occurring within the extensions rather than the original window, could imply that the extrema are not due to irregular gait.

In the case that the minimum is outside the original window, but inside the extended environment, it is optionally further examined by a different window. After establishing that it is indeed an abnormality that exists within the window, a closer examination, around the suspected misstep, is optionally performed to determine if it is a misstep or not. For that a smaller window may be built around the beginning point of the misstep (BPMS). Since the time before that point is less relevant than the time after it, which may include a recovery mechanism, the optionally window is built by taking 1.25 sec before the BPMS and 2.5 sec after it.

In the new window the 2 lowest minima are detected. If the higher minima times 1.3 is greater than the lower minima than it is declared as not a misstep by this feature.

A similar procedure is optionally performed for all the 6 features described above and their decisions enters a Majority Rule decision module (for example). If 3 or more of the features declare the window as a misstep than it is labeled as such.

This method appears to detect most of the missteps, but also reports some false alarms. Optionally, at least some of the false alarms are filtered out by using 2 thresholds. The first is a requirement that a filtered signal of V acceleration exceeds the value of (for example) 0.4 (Band pass filter 0.5-4 Hz) and the second is that the filtered ML-Gyro exceeds the value of (for example) 25 (Band pass filter 4-20 Hz).

Results

Running this algorithm on laboratory data achieves 71.7% Hit ratio and 96.3% specificity. It should be noted that Hit ratio is used instead of sensitivity because missteps may occur over more than one window and for this method detection of at least one of them is sufficient.

SFA

Description

In an exemplary embodiment of the invention, gait detection, for example as described above is optionally applied to the laboratory data to automatically detect segments of gait.

A running window of (for example) 5 seconds is computed for (for example) 6 signals. At each window a series of features are calculated for each subject and a feature vector is created. For each feature vector the maximum is detected and points which exceed a threshold, derived from that value, are marked. It should be noted that although the thresholds are computed by the same computational method for all subjects, the resultant threshold value differs.

In an attempt to improve the specificity, various features were extracted from the signals, as will be described below. In total, over 60 features were extracted from the 3 axes of acceleration and the 3 axes of gyroscopes. The features included parameters from time and frequency domain including wavelets and statistics. Eventually, only a few of these features were utilized. The features are:

Acceleration Features

The acceleration features are root mean square (RMS) of AP acceleration and the signal vector magnitude (SVM) of 3-axes standard deviation, SD. Extreme changes in those two features indicate irregularity in the gait.

Frequency Features

These features are divided into 2 parts—features extracted from gait frequency (0-3 Hz) and from higher frequencies (3-10 Hz) at which missteps may be observed.

ske5W=Skewness of the ML-Gyro in gait frequency
ske1M=Skewness of the V-Acceleration in High frequencies
ske2M=Skewness of the ML-Acceleration in High frequencies
kur2W=Kurtosis of the ML-Acceleration in gait frequency
kur5W=Kurtosis of the ML-Gyro in gait frequency
kur2M=Kurtosis of the ML-Acceleration in High frequencies DWT Features There are several families of DWT, here used is the 2nd level of 'db4'-cAA.

The discrete wavelet features that were used are:
DWTkur2=Kurtosis of the ML-Acceleration
DWTkur3=Kurtosis of the AP-Acceleration
DWTkur5=Kurtosis of the ML-Gyro
DWTkur6=Kurtosis of the AP-Gyro
DWTske3=Skewness of the AP-Acceleration
DWTske2=Skewness of the ML-Acceleration
DWTske5=Skewness of the ML-Gyro Three methods are optionally used for calculating thresholds. Different methods may be used for different features. Optionally, all the methods are based on finding global peaks for each subject. The formulae used for each threshold are:
Threshold 1=amplitude of the 4th strongest peak
Threshold 2=amplitude of the 2nd strongest peak
Threshold 3=1.25*(mean+std)

For example, Threshold 1 is used for RMS of AP (RMS-AP), threshold 2 is used for STD 3D and Frequency features, and threshold 3 is used for DWT features.

By analyzing an SVM of 3-axis standard deviation SD it is possible to see that this feature can separate well missteps from non-missteps and using thresholds it is possible to reject many examples which are not missteps. Optionally, the threshold is on the distance from the origin.

Marked windows from those features are labeled as "suspected missteps". Union between these features detect the majority of missteps (over 90%) but also results in many false alarms (FA). To identify missteps with higher certainty additional features such as skewness and kurtosis are optionally used by applying the same mechanism. These features were chosen because they can identify many of the FA while almost not returning any hits. The following table shows the features' performance:

| Feature | Hit ratio | Specificity | FA |
| --- | --- | --- | --- |
| RMS-AP | 67.85 | 95.34 | 151 |
| STD3D | 89.28 | 91.28 | 295 |
| RMS-AP + STD3D | 96.43 | 90.3 | 329 |
| ske5W | 3.57 | 95.78 | 136 |
| ske1M | 0 | 96.41 | 115 |
| ske2M | 0 | 96.53 | 111 |
| kur2W | 0 | 96.77 | 103 |
| kur5W | 7.14 | 95.93 | 131 |
| kur2M | 0 | 96.47 | 113 |
| DWTkur2 | 0 | 93.49 | 215 |

-continued

| Feature | Hit ratio | Specificity | FA |
| --- | --- | --- | --- |
| DWTkur3 | 0 | 90.61 | 320 |
| DWTkur5 | 0 | 92.15 | 263 |
| DWTkur6 | 3.57 | 90.14 | 338 |
| DWTske3 | 0 | 86.43 | 485 |
| DWTske2 | 0 | 88.74 | 392 |
| DWTske5 | 0 | 87.46 | 443 |

The union of the first two features, RMS-AP and STD3D, is used to label windows as "suspected missteps" and union of the other features is used to reduce FA.

Results

Running this algorithm on laboratory data achieved 85.7% of Hit ratio and specificity of 95.4% and FA of 147.

Anticipatory Postural Adjustment

In an exemplary embodiment of the invention, it is expected that a subject makes anticipatory postural adjustments (APAs), for example, changes in center of gravity (COG) and center of pressure (COP). Optionally, such APAs are detected, for example, using cameras and/or movement sensors and used, for example instead of or in addition to other physiological measures, to predict and/or identify gait abnormalities such as FOG.

In an exemplary embodiment of the invention, an APA is measured by quantifying the COP and/or by measures of trunk movements using accelerometers and/or gyroscopes carried on the belt or other positions that allow for estimation of the COP and/or COG. By challenging the subject in the VR system, it may be possible to detect early, mild and/or subclinical APA disturbances which may also optionally be used as markers for FOG. As noted herein, early detection allows to implement an early and potentially protective interventional approach to delay, reduce and/or prevent FOG and/or other functional disorders.

In an exemplary embodiment of the invention, APA detection is used for driving a cueing system for treatment of FOG and/or other gait disorders.

In an exemplary embodiment of the invention, APA detection is used as a marker for the usefulness of interventional programs with drugs, deep brain stimulation or physical rehabilitation methods.

In an exemplary embodiment of the invention, APAs are used to predict FOG, for example, before turns, when starting to walk and/or even during "open runway", usual walking.

In an exemplary embodiment of the invention, APAs are used as a target of training, for example, after training, larger APAs may be expected for some patients.

In an exemplary embodiment of the invention, APAs are used to diagnose a patient, for example, by seeing if and how APAs change and/or are delayed as a function of the type or other parameter of challenge used.

In an exemplary embodiment of the invention, VR simulations are modified in real-time to cause a desired APA (e.g., a certain COP). Optionally, the simulation is modified (e.g., various scenarios tried, intensity changed) until a desired APA is detected and/or failure is decided.

The abstract of Exp Neurol. 2009 February; 215(2):334-41. Knee trembling during freezing of gait represents multiple anticipatory postural adjustments. Jacobs J V, Nutt J G, Carlson-Kuhta P, Stephens M, Horak F B reads as follows: Freezing of gait (FoG) is an episodic, brief inability to step that delays gait initiation or interrupts ongoing gait. FoG is often associated with an alternating shaking of the knees, clinically referred to as knee trembling or trembling in place.

The pathophysiology of FoG and of the concomitant trembling knees is unknown; impaired postural adjustment in preparation for stepping is one hypothesis. We examined anticipatory postural adjustments (APAs) prior to protective steps induced by a forward loss of balance in 10 Parkinson's disease (PD) subjects with marked FoG and in 10 control subjects. The amplitude and timing of the APAs were determined from changes in the vertical ground-reaction forces recorded by a force plate under each foot and were confirmed by electromyographic recordings of bilateral medial gastrocnemius, tibialis anterior and tensor fascia latae muscles. Protective steps were accomplished with a single APA followed by a step for control subjects, whereas PD subjects frequently exhibited multiple, alternating APAs coexistent with the knee trembling commonly observed during FoG as well as delayed, inadequate or no stepping. These multiple APAs were not delayed in onset and were of similar or larger amplitude than the single APAs exhibited by the control subjects. These observations suggest that multiple APAs produce the knee trembling commonly associated with FoG and that FoG associated with a forward loss of balance is caused by an inability to couple a normal APA to the stepping motor pattern.

In an exemplary embodiment of the invention, APAs are measured using a force platform and/or using center-of-pressure dynamics (e.g., force sensitive insoles or the accelerometers described above, which can reflect movement of the body's center-of-mass, which will reflect also the APA).

The inventors have also discovered that, based on a study 29 patients with Parkinson's disease (PD), freezing of gait episodes during turns are marked by multiple failed postural adjustments. These postural adjustments are typically seen as Anticipatory Postural Adjustment at gait initiation (e.g., before the person starts to walk). However, using measures of Center of Pressure (COP) Dynamics, they can also be quantified during turning and/or during straight line walking.

The obstacles placed in front of the subject generally also require a form of an APA (e.g., shifting of the center of gravity from one foot to the other to allow for sufficient clearance of the virtual obstacle). By challenging the subjects with these virtual obstacles (e.g., of different lengths and/or heights), the APAs/COP in response (e.g., before and/or during) can be measured. Possibly, in a healthy subject, the APA size will be related to the size/height of the obstacle. Optionally or alternatively, if/how these APAs change during FOG is measured. This can give another measure of FOG pre-disposition and possibly further enhance the ability to grade FOG severity, to predict, and/or to measure the response therapy.

In an exemplary embodiment of the invention, APAs are treated as are other measures, such as BCG. For example, APA is included as one of the weighted features in the scoring for FOG.

It is noted that in some embodiments, the APAs are measured on the ground (e.g., if patient is walking on ground towards a very large screen and/or wearing goggles) and in other embodiments APAs are measured on motion devices, such as treadmills and/or bicycles.

In an example of on ground VR display, a patient follows a standard lab course, such s walking along a corridor, and goggles are used to inject obstacles into the course and/or provide other loads as described herein.

Quantifying Fall Risk

The Fall Risk score is a composite measure optionally based on two or more of the number of events detected by the system during the test, gait parameters reflecting abnormal patterns (e.g., stride time variability (CV), PCI, symmetry), the response to the VR provocations, number of errors on obstacle crossing, the cost of environmental features (e.g., determined as stride time in trial 3—stride time in trial 4) and/or the cost of cognitive load on performance (e.g., determined as stride time in trial 5—stride time in trial 4).

Table 1 (FIG. 6) shows how such a composite score is optionally calculated. The composite score described herein provides the subject with an overall, composite score, based on the combination of multiple components. In addition to this single summary measure, the clinician may receive more detailed information that describes fall propensity based on performance in the VR system. Using a weighted analysis, all measures are optionally assessed under 4 levels (or a smaller or larger number of levels): gait changes, cost and provocations, obstacle avoidance, adaptation. Each of these levels optionally receives a separate score and then all levels may be evaluated to provide a fall risk score based on, for example, a 4 point Likert scale.

It is noted that in other methods, fall risk is not quantified and is described based on either clinical performance based measures such as the timed up and go (in which a person's performance is considered high risk or low risk) or on measures of gait which can reflect a problem and a risk for falls that is specific to gait (high gait variability). In an exemplary embodiment of the invention, the multifaceted levels that increase the risk of falls and therefore the definition of risk is taken into account. In some embodiments of the invention a multifactorial definition is used which takes into consideration many levels of risk. For example, high risk is identified as frequent changes in gait pattern or detected missteps even with situations with low level provocation, or simple environments, and a deterioration in gait pattern in response to even simple cognitive challenges resulting in high gait variability and asymmetry.

In an exemplary embodiment of the invention, the score is a linear sum of considerations, each weighted, for example, according to patient characteristics, for example, based on a library of control subjects. Other forms of score formula may be used as well.

While not limited to the following definitions, some embodiments of the invention define a fall as 'unintentionally coming to the ground or some lower level and other than as a consequence of sustaining a violent blow, loss of consciousness, sudden onset of paralysis as in stroke or an epileptic seizure' (Kellogg 1987). In an exemplary embodiment of the invention, a misstep or near fall is defined as a loss of balance or foot hold with the ground during gait which did not result in a fall due to the ability to overcome it/control it/compensate for it. In an exemplary embodiment of the invention, the use of a harness prevents actually falling but allows falls and missteps to be estimated based on trajectory before harness stops patient and/or based on change in gait pattern (e.g., including the higher frequency) can indicate that the pattern is of a misstep.

Experiment

The above-described implementation was used in an experimental study, as described below and shows the ability of the proposed VR system, in accordance with some embodiments of the invention (e.g., FIG. 4A-FIG. 5) to provoke and detect fall episodes under safe environmental conditions. The system is able to provoke fall episodes on the treadmill. The system is able to sensitively detect these fall episodes, and using the system features is able to quantify and/or configure a severity score that can be used to diagnose and later provide care to patients with risk of or existing fall events. It is noted that features described with the experiment may be used, as desired with other embodiments of the invention from the one used in the experiment.

Participants

The developed system was tested on 3 healthy elderly subjects with a history of falls (mean age 71.7±7.5 yrs) and one healthy older man (67 yrs) with no history of falls who served as a control subject. All subjects reported no distinct medical history that may have contributed to the occurred falls, they were all community ambulators and were independent in activates of daily living. Participants were excluded if they had substantial cognitive deficits (scored <21 on the Montreal Cognitive Assessment scale), unstable heart disease or suffered from severe depression.

Procedures

After signing an informed consent, demographic information and medical history were collected by a researcher. Prior to testing the system, a baseline assessment was conducted to evaluate gait over ground. Gait speed was measured over 10 meters. This information was imperative as the treadmill speed during the system's evaluation was set for each participant based on their over ground walking speed. In other embodiments, speed may be set during trial and/or matched to an actual walking speed on a continuous and/or semi-continuous basis. Participants were then fitted with the sensors (Shimmer, Nexus and fNIRS) for testing with the system. The test included 5 walking conditions each of 4 minutes for a total of 20 minutes of walking. Rest breaks were given between the trials. The trials varied with each walking condition focusing on a different component that may influence gait and fall risk.

Trial 1—Difficult: high level of difficulty, maximum amount of obstacles, maximum amount of challenging scenarios (tunnels, cave, bridges, and narrow passages)

Trial 2—Moderate: medium level of difficulty, moderate amount of obstacles, minimal amount of challenging scenarios, low environmental complexity Trial 3—Environment: high level of difficulty, moderate amount of obstacles, minimal challenging scenarios, high environmental complexity (obstructed visibility, night)

Trial 4—Gait challenges: low level of difficulty, no obstacles, maximum challenging scenarios (tunnels, caves, bridges and narrow passages)

Trial 5—Cognitive: high level of difficulty, moderate amount of obstacles, low amount of challenging scenarios, additional cognitive task (on top of walking with the VR simulation, the participants were asked to perform a verbal fluency task).

In an exemplary embodiment of the invention, these specific trials/levels were chosen as they cover the most common causes for missteps and falls (e.g., tripping/environmental, gait impairments, cognitive and sensory motor integration). The parameters in each of the trials could be quantified (i.e., number of obstacles placed, the distance between them, frequency of appearance, number of provoking challenges etc). The number of provocations and obstacles within a 4 minute trail depends on the speed the subject is walking in and can vary on average, for example, between 25-40 (when gait speed is between 0.8 cm/s-1.4 m/s and an obstacle is placed on average every 6 steps).

Validation with Physiological Measures that Possibly Contribute to Fall Risk

The following methods were used in order to validate the detection algorithms and to also assess several physiological measures that have a role in falls.

a. During the tests, an experienced clinician observed the subject and annotated any missteps that occurred. The report included both descriptive measures of severity and time of event. In addition, all trials were videotaped. Another experienced researcher was asked to review the recorded videos and annotate time of misstep events based on the video recordings. These were then compared to the events detected by the system and by the researcher who attended the tests.

b. Miniaturized physiological sensors (NeXus MindMedia BV the Netherlands) were attached to the person's chest to monitor the person's heart rate (HR) during different scenarios and walking conditions and physical and mental stress to try and identify if any changes occurred that could indicate an event. As some falls occur due to syncope, optionally, these sensors can also be used to aid the clinician in the diagnosis and evaluation of possible risks for falls in particular individuals. The wireless NeXus sensors transmitted data in real-time to a computer using Bluetooth technology. Using designated software, heart rate and inter-bit-intervals were extracted from the data collected by the sensors in all gait trials.

c. Wireless functional Near Infrared Spectroscopy (PortaLite, Artinis, The Netherlands) was used to assess changes in frontal lobe blood flow during gait to shed light on cognitive function during challenging situations that increase the risk for falls. The system uses Near Infrared Spectroscopy to measure local tissue saturation as well as oxy, deoxy and total hemoglobin concentrations in the frontal lobe during activity. Oxy and deoxy hemoglobin data (in units of micromole/liter) during all gait trials were extracted using Matlab software. As noted, optionally, these sensors can also be used to aid the clinician in the diagnosis and evaluation of the possible causes of increased risk of falls in a particular participant such as cardiac syncope, arrhythmias and subtle cognitive impairments (e.g., as observed by decreased frontal lobe blood oxygenation).

Data from both HR and FNIRS were examined throughout the gait trials and changes and events were assessed and verified according to the video recordings. The signals were then examined for an interval of 10 seconds before and after a detected event to observe any changes in activation. The signals were then compared to no-event and no-obstacle trials.

Data Analysis

Data was examined for normalcy and descriptive statistics were extracted for all gait measures. Validation data were analyzed based on time series across all detected events. Quantification data were analyzed for each person as a case study.

Results

Diagnostic Capabilities

Three healthy older adults with a history of falls and one control participant participated in this study designed to demonstrate diagnostic capabilities. The three participants reported falling at least twice in the year prior to the study rendering them as "multiple fallers." All participants were functionally active and living in the community. Table 2 (FIG. 7) provides the subject's descriptive characteristics. It should be noted that subject number 2 is the control participant (no history of falls).

Gait Data

Figure 8:
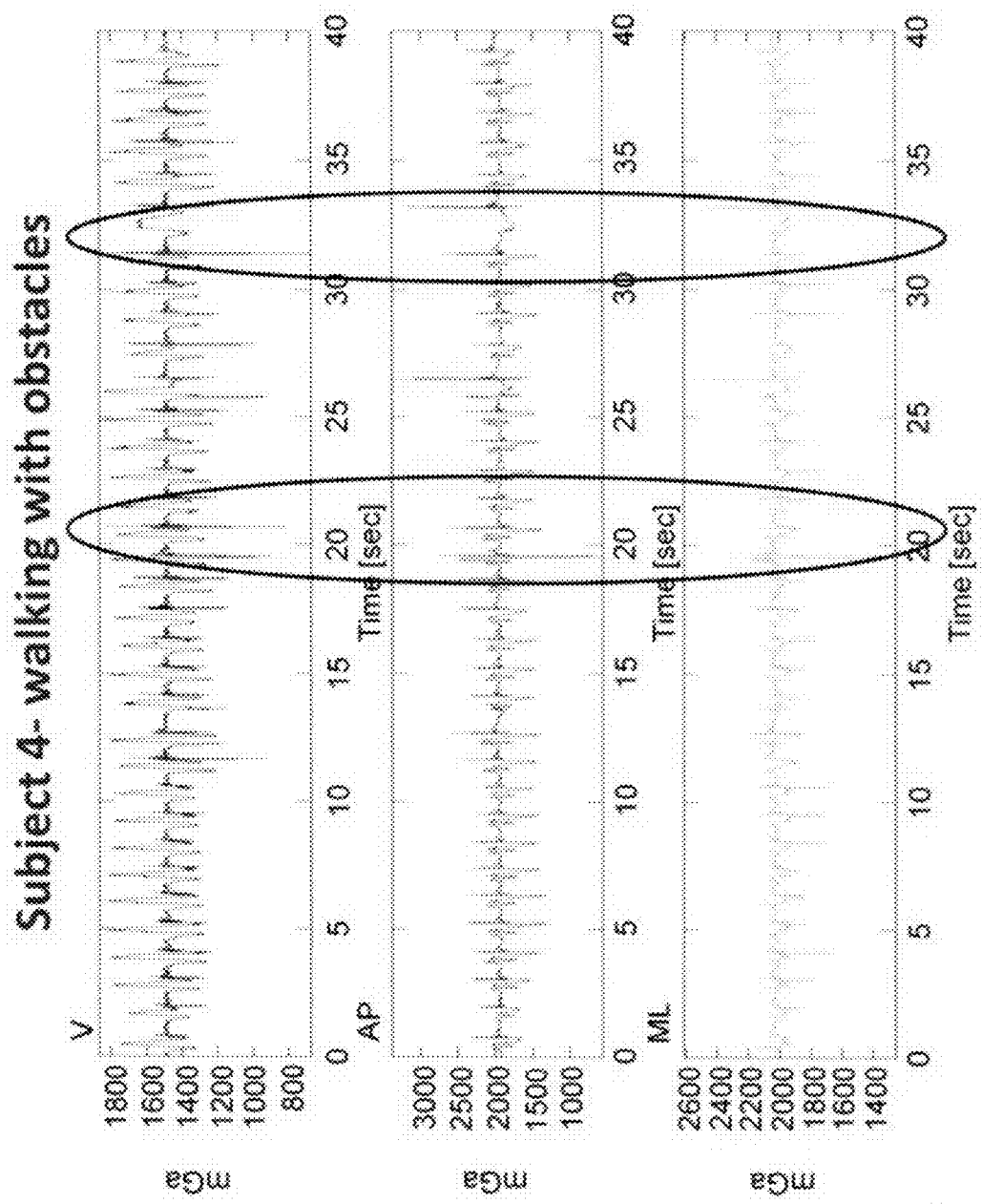
FIG. 8 shows acceleration signals of a subject during an obstacle trial, in accordance with exemplary embodiments of the invention.

Mean gait speed during over-ground walking was 1.4±0.1 m/s. Gait speeds on the treadmill were set 20% slower to allow for obstacle negotiation as well as try to induce misstep events. Treadmill speeds ranged between 1.1-1.2 m/s and were not changed between the different trials, to maintain consistency of gait and evaluate strategies of walking in the different conditions. FIG. 8 demonstrates the acceleration signal of the gait of subject 4 during the obstacle condition (trial 1). The top graph represents the signal collected in the anterior-posterior axis (AP), the middle signal represents the movement in the vertical axis (V) and the bottom signal represent movement in the medio-lateral direction (ML). The ellipses circles are examples for location of obstacles within this time frame. It should be noted that the acceleration increases when the person attempted to cross the obstacle. In the ellipse on the right the subject was attempting to cross a horizontal obstacle, which increased his step.

Average stride time in the no-obstacle condition was 1.21±0.42 sec for the fallers and 1.16±0.31 for the control subject. Stride time did not change during the obstacle conditions (1.23±0.63 sec and 1.24±0.58 sec). However during the challenging walks (environmental complexity and cognitive load), all participants demonstrated shorter stride time (1.15±0.45 sec and 1.14±0.61 sec respectively), suggesting a compensatory strategy in challenging situations.

The costs of adding obstacles, environmental features or a cognitive task were calculated as the difference in stride time between the no-obstacle conditions and the evaluated condition (environmental/cognitive/obstacle). The three fallers demonstrated the largest differences in the cognitive task, which could be considered as the 'dual task' effect (0.53 sec) however, interestingly the control participant did not show a dual task effect with only a difference of 0.07 sec in stride time between the trials. In the environmental challenge condition, the participants were asked to walk in a dark environment with low visibility. Here all 4 participants demonstrated the same effect with a decrease in stride time of an average of 0.19 sec. These findings suggest that during decreased visibility walking, older adults change their walking pattern to reflect a more cautious pattern, which could perhaps be considered a coping strategy for a difficult situation. These findings may also reflects the difficulty that older adults have in these situations that could increase fear of falling and result in individual restrictions of movement in these situations (such as not going out at night, not getting up during the night because of the fear of falling in the dark etc.) By identifying such a behavior of difficulty one can provide treatment and interventions to relieve such fears and improve performance and confidence in walking. The findings also support the reports in the literature that fallers have more difficulties with DT tasks.

A symmetry ratio was calculated as the difference in stride time between the sensors worn on the right and left legs during the no obstacle condition and reflected as percent. This ratio reflects a difficulty in controlling gait evenly on both legs. Participants 1, 2 and 4 demonstrated an almost perfect symmetry (98%, 99% and 98% respectively). Subject 3 demonstrated a high inter-limb asymmetry with a ratio of only 50% suggesting a less coordinated gait. This possibly reflects dis-coordination or weakness of one side which could result in increased risk of falls.

Measures of consistency in walking were also evaluated. Coefficient of variation (CV) and PCI were calculated from the gait during the no-obstacle condition. For both measures, the closer the values were to zero, the more consistent the gait rhythm, suggesting a less impaired gait pattern with more intact bilateral coordination. In addition, the amplitude and width of the dominant frequency throughout the 4 minute no-obstacle walk were examined using spectral analysis. In table 3 (FIG. 9), are presented the results of the 3 subjects compared to the control subject. A sharper and narrower peak reflects a more consistent, rhythmic, and healthier gait pattern, i.e., reduced gait variability and lower stride-to-stride fluctuations.

Figure 10:
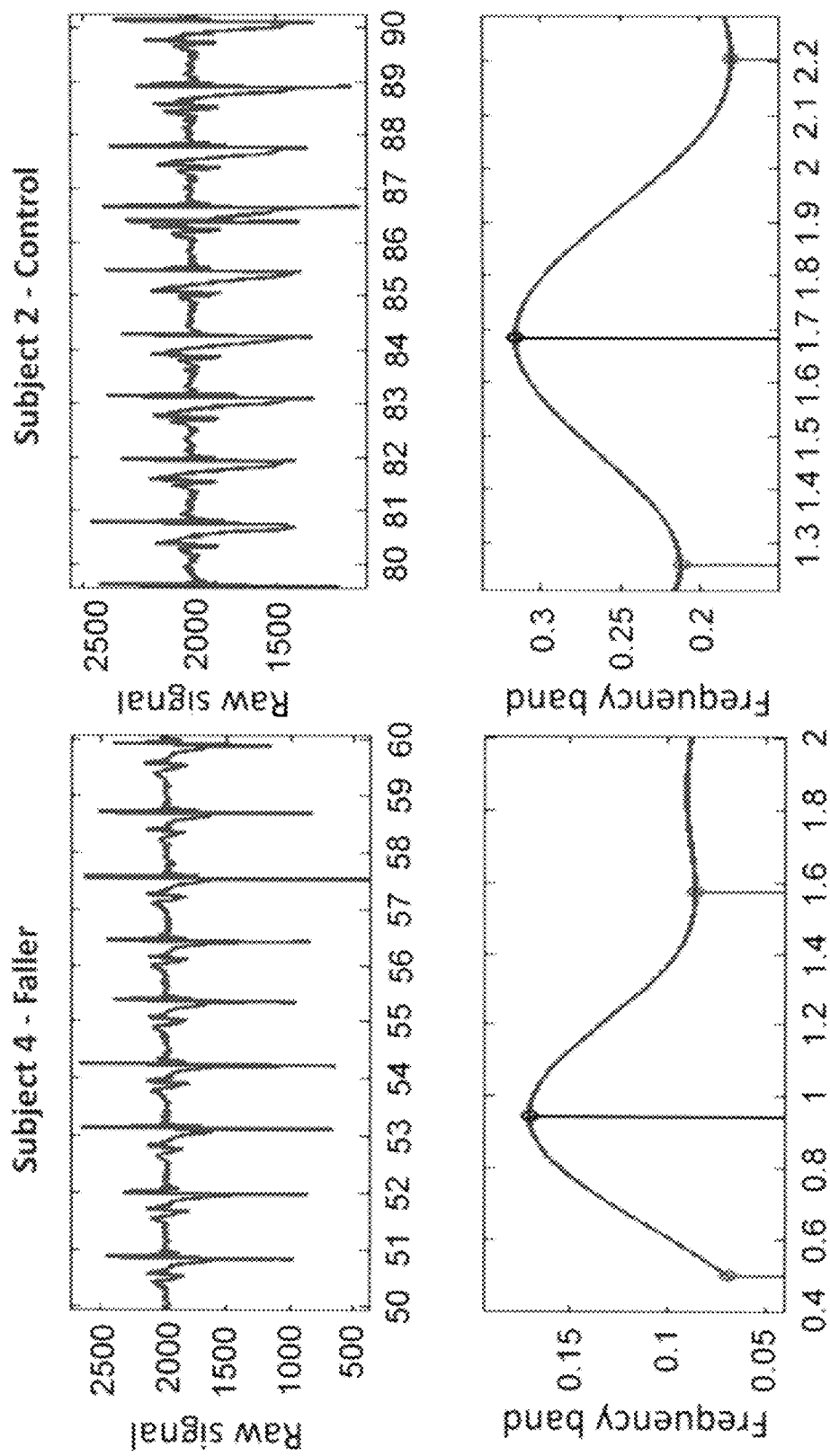
FIG. 10 shows a raw acceleration signal and spectral density of the frequency band of the gait of a faller compared to a control participant, in accordance with exemplary embodiments of the invention.

FIG. 10 shows a raw acceleration signal and spectral density of the frequency band of the gait of a faller (subject 4) compared to the control participant (subject 2). Note the higher amplitude and narrower signal in the control subject then subject 4 (faller) suggesting a more controlled and less variable gait pattern. The signals represent 10 seconds of gait in the no-obstacle trial. The effects of the various challenging conditions on these measures can also be included as another measure of fall propensity.

Gait Abnormalities and Misstep Detection

A total of 31 events were detected by the system; 6 of those events were deemed as missteps by using the video recordings. Sixteen of the 31 events collected were recorded during the trials of subject 4. All events reflected changes in frequency of the signal during walking within the window stipulated by the FFT. In further analysis these changes reflected missteps but also increased steppage gait when crossing obstacles, overshooting and undershooting targets, and irregular steps produced as compensation for challenges presented by the system. All events lasted less than 2 seconds, perhaps because of the continuous motion of the treadmill belt and the need for the subjects to take a step forward. This may predispose patients to take larger steps and have legs moved by treadmill and thus avoid falling. Nonetheless, even on the treadmill, with virtual obstacles, missteps could be reliably provoked.

Figure 11:
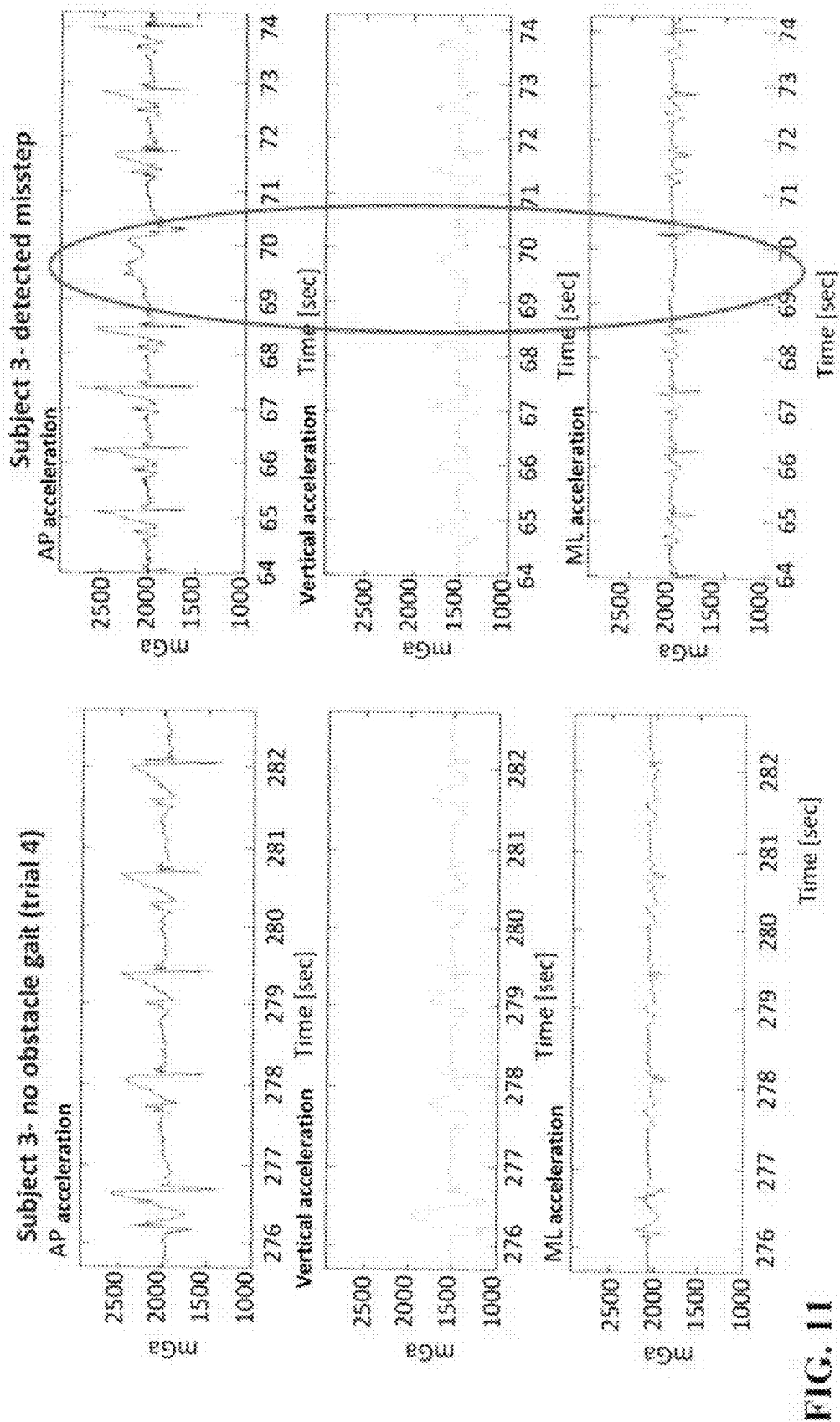
FIG. 11 shows an acceleration signal of the gait of a subject during a no-obstacle condition and the signal from a cognitive trial in which a misstep is detected, in accordance with exemplary embodiments of the invention.

FIG. 11 shows the acceleration signal of the gait of subject 3 during the no-obstacle condition (trial 4) and the signal from the cognitive trial (5) in which a misstep was detected. The top graph represents the signal collected in the anterior-posterior axis (AP), the middle signal represents the movement in the vertical axis (V) and the bottom signal represent movement in the medio-lateral direction (ML). The ellipse indicates the misstep detected by the system.

Validation

Events detected by the sensors were compared against the recordings done by the researcher in the test and the identification of events using video recordings. There were 31 events detected by the system, 27 of those were corroborated by the researcher observing the tests. From the videos, only 26 were deemed as gait corrections over obstacles, missteps or changes in gait pattern that could result in a fall if not supported. Although the events were very short and some were not easily observed on the video, there was a high agreement between the researchers and the automated system. This finding is encouraging as it demonstrated the high sensitivity and specificity of the system.

Figure 12:
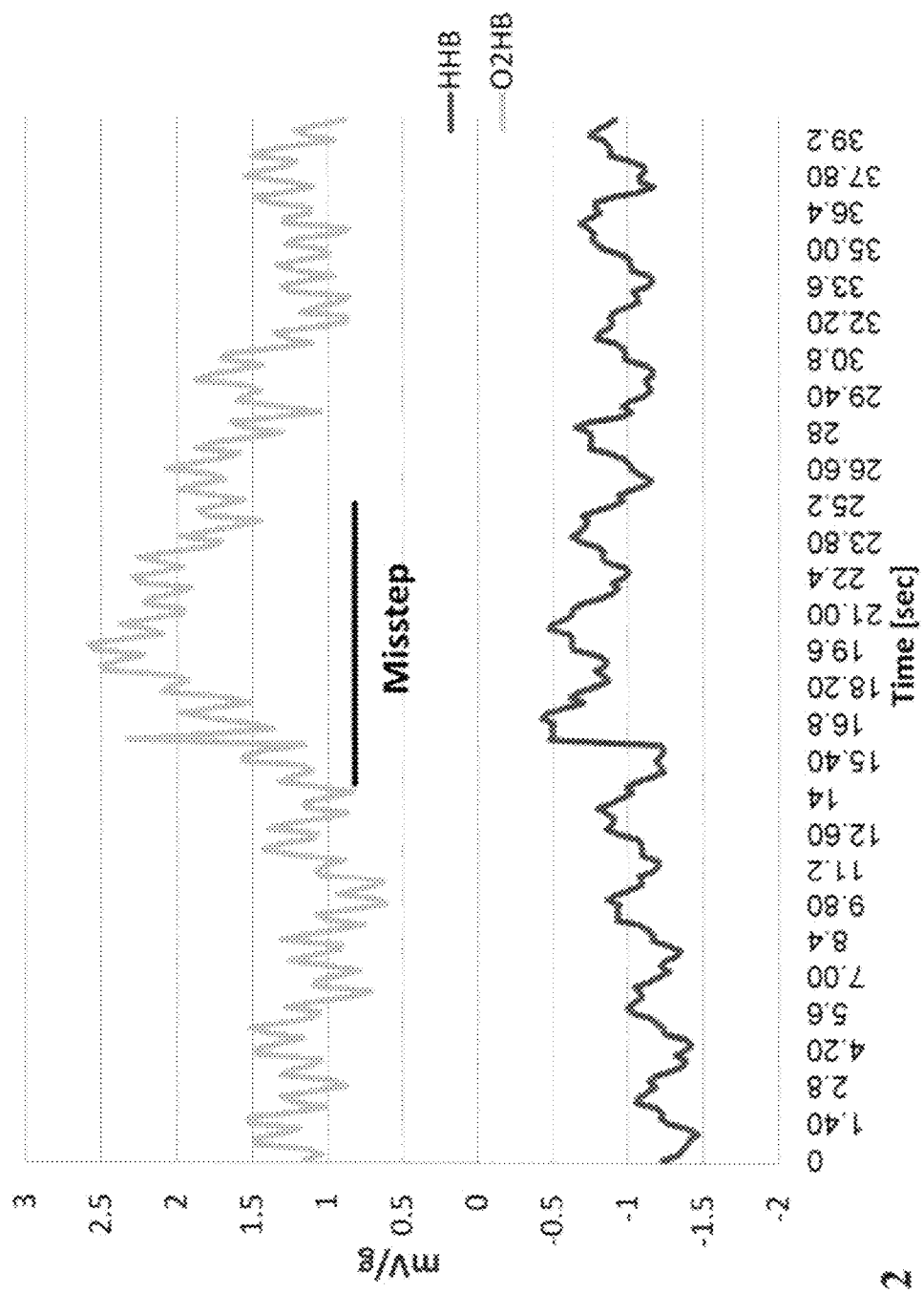
FIG. 12 shows a raw signal from an fNIRS sensor including a misstep event, in accordance with exemplary embodiments of the invention.

To further validate the system, physiological measures (e.g., fNIRS and HR) were used as well. FIG. 12 shows the raw signal from the fNIRS and demonstrates the raw signal from the fNIRS during a misstep event. The light line represents de-oxy hemoglobin and the dark line represents oxy hemoglobin. The time series reflects 40 seconds of gait. The increase in oxy hemoglobin in the frontal lobe during the event may suggest that the brain is circumventing blood flow to the frontal lobe in order to motor plan a strategy of recovery from the event. When the misstep occurs, there is an increase in blood flow in the frontal lobe. The increase blood flow may be a reflection of the need for cognitive awareness and planning a recovery strategy to quickly come into play.

Figure 13:
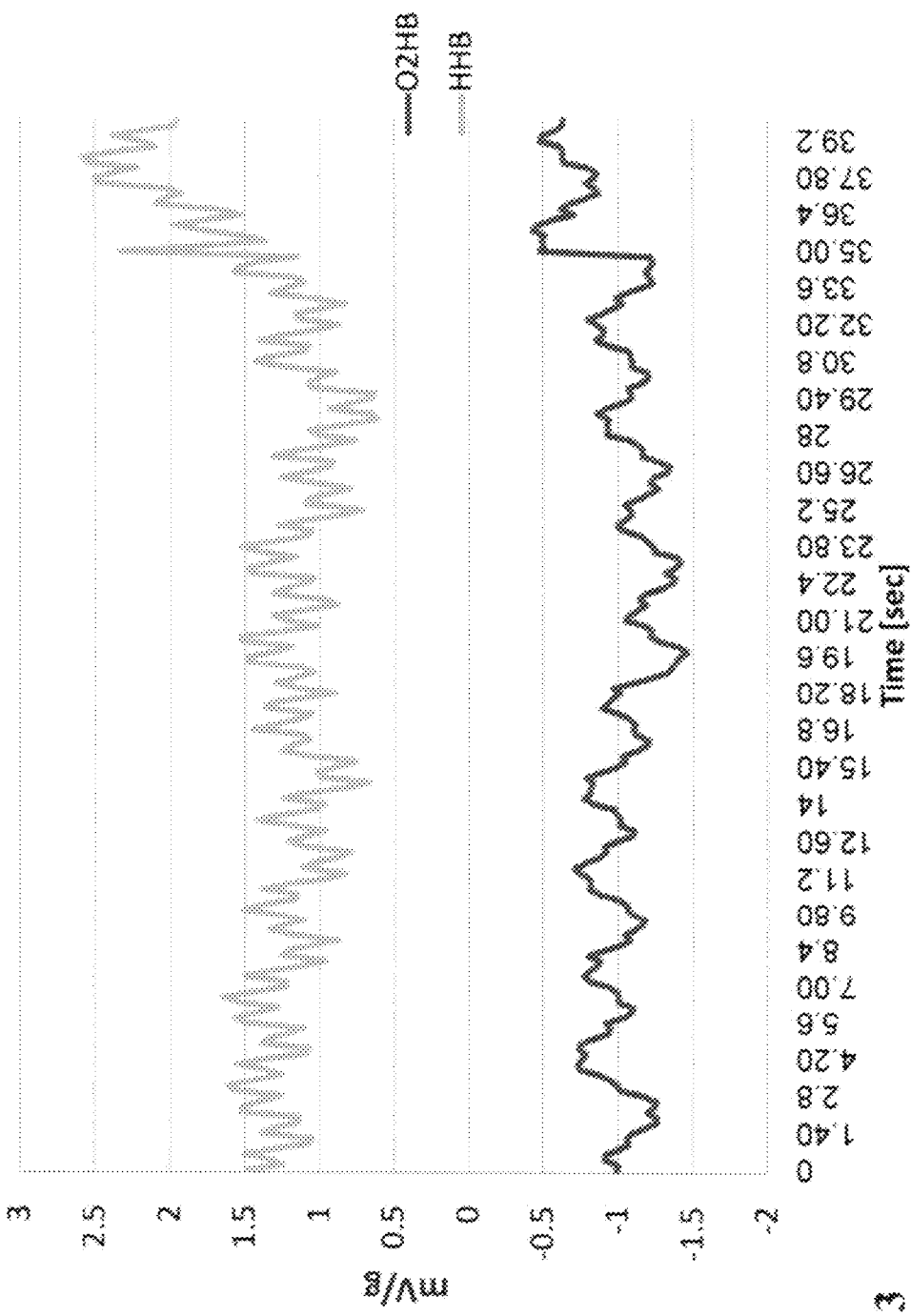
FIG. 13 shows a raw fNIRS signal during a time period when no misstep is detected, in accordance with exemplary embodiments of the invention.

This pattern was not observed during normal gait or during the negotiation of obstacles. For example, FIG. 13 shows a raw signal from the fNIRS during trial 1 (obstacles) with no misstep detected. The light line represents de-oxy hemoglobin and the dark line represents oxy hemoglobin. The time series is 40 seconds long. Note the sinusoidal rhythm reflects the pattern of walking and corresponds to heart rate measure. Optionally, the fNIRS signal is used to provide information regarding, for example, heart rate and/or gait variability.

Figure 14:
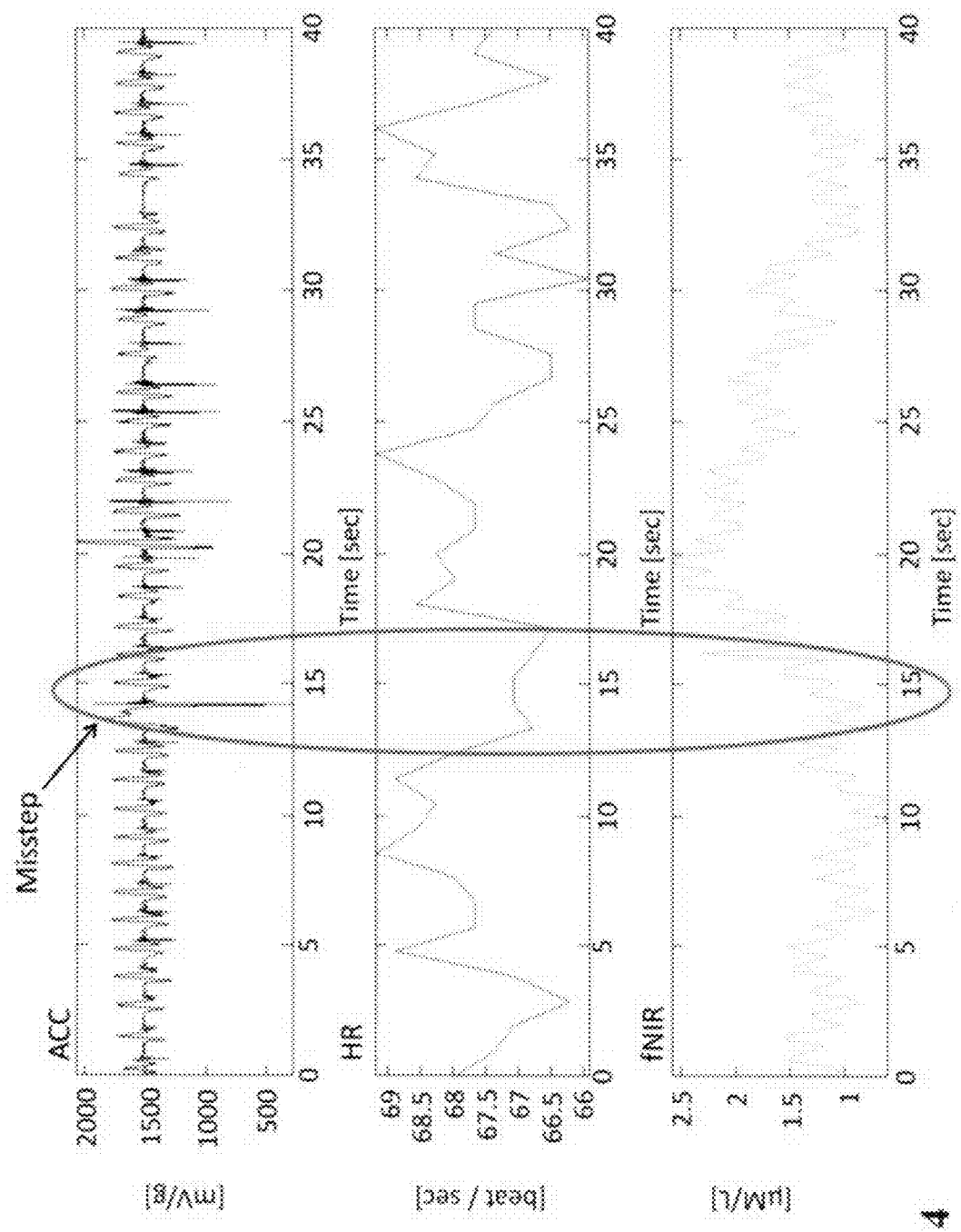
FIG. 14 shows the signals from three physiological sensors, in accordance with exemplary embodiments of the invention.

In addition, a correlation between changes in acceleration signal and changes in physiological measures was assessed. FIG. 14 combines all 3 measures and provides an indication that gait challenges can be reflected in physiological measures even when the event is short in duration and the gait is executed on a treadmill. As shown in FIG. 14, information from all 3 physiological sensors is combined. The top signal is the acceleration. The ellipse reflects the time the system detected the misstep. The middle signal reflects the heart rate extracted from the NeXus and the signal box shows the oxy-hemoglobin signal from the fNIRS. Note the changes in all 3 signals during the event. After the event there was an increase in both heart rate and blood flow to the frontal lobe with a delay of, for example, 3-5 seconds.

Quantification

In an exemplary embodiment of the invention, fall risk score is a composite measure based on two or more of the number of events detected during the test, gait parameters reflecting abnormal patterns (e.g., CV, PCI, symmetry) associated with fall risk, the response to the VR provocations, number of errors on obstacle crossing, the cost of environmental features (determined as the difference in stride time between trial 3—trial 4) and/or the cost of cognitive load on performance (the difference in stride time between trial 5—trial 4) (see table 2, FIG. 7). Using a weighted analysis, a score was provided on a 4 point Likert scale. The fall risk score as determined using the system for each participant is presented below.

Subject 1

MW is an 83 year old woman with a history of 2 falls in the past year (one of which resulted in an injury to her wrist). She reports that she feels unstable and has difficulty in crowded places to the point she tries to avoid going out. A total of 3 events were detected by the system during all of trials, 2 were validated by the researchers suggesting a relatively low risk of falls. In some patients a target number of falls or near-falls is set, for example, 3, 10, 50, 100, or other numbers and/or a misstep rate, for example, 1 in 10,000 steps, 1 in 25,000 steps, 1 in 100,000 steps, 1 in 200,000 steps or smaller, intermediate or larger frequencies. The number of steps and/or challenges may be adjusted to achieve such a desired rate and/or statistical significance thereof. The gait events mainly occurred during the difficult trial and while environmental challenges were added. MW walks with a very low clearance gait and often her gait appears as shuffling. 67% of the errors made on obstacle crossing were secondary to low clearance which increases the risk for falls. Table 4 (FIG. 14) summarizes the results of her tests.

Subject 2

EB is a 67 year old man with no history of falls. EB served as our control subject. He is retired and has sustained a mild MI a year ago. EB is physically fit and walks 4 km everyday. He is cognitively intact but reports forgetfulness on occasion. A total of 5 events were recorded by the system. Two of those were deemed by the researcher as changes in the gait pattern that are not of a corrective nature. The most difficulty EB had was in the cognitive trial, where 2 events were recorded and where most of his mistakes occurred. In the VF task, the subject was able to recall only 5 words within 4 minutes. Therefore although he came into the study as a control subject, EB actually has a non-zero, mild risk of falls (mainly due to in attention) and could benefit from DT training within the VR consisting of walking while navigating in a VR environment rich with stimulus and attention demanding situations. Optionally, the therapist provides specific strategies to follow or they are presented on the VR system. Optionally or alternatively, the patient is allowed to formulate his own strategies, optionally with the system generating a signal if the strategies are less desirable (e.g., walking speed below a threshold value, shuffle steps). Table 5 (FIG. 15) summarizes the results of his tests.

Subject 3

EB is a 68 year old woman with a history of 2 falls in the past year. A total of 7 events were recorded during the trials. Most of the events were due to inability to cross the obstacles (specifically the hurdles) as EB demonstrated a highly variable stepping pattern. In addition, the added provocations decreased her ability to negotiate the obstacles. EB's gait was found to be asymmetrical and highly variable adding to her fall risk score. The specific findings of asymmetry may help prescribe a treatment for her to increase symmetry, improve control on the more effected limb and hence improve performance. Table 6 (FIG. 16) Summarizes the results of her tests.

Subject 4

AB is a 69 year old male with a history of 4 falls in the past year (2 injurious). As per self report, his falls occur because of tripping over things. The system detected 16 events during the trials. Most of the events were due to inability to negotiate obstacles and 2 of the events were deemed as missteps. However AB also demonstrated difficulty in the cognitive trial with a high DT cost, and high variability of gait therefore this patient may likely benefit from an intervention consisting of walking while navigating in a VR environment rich with stimulus and attention demanding situations. All these measures combined to produce a high risk of falls score. Table 7 (FIG. 17) Summarizes the results of his tests.

Results of Therapeutic Application

Further experimentation tested the idea of treatment based on diagnosis and/or controlled level of challenges. Without being limited to a specific hypothesis, it is possible that that motor learning principles and/or bio-feedback can modify the locomotion strategies employed by subjects who are prone to falling so that they will now be able to avert/reduce/recover from and/or otherwise assist approaching and/or ongoing fall/misstep episodes. Possibly, the central nervous system (CNS) will be trained to modify the gait pattern in situations that typically cause falling and/or near falls and/or in general mobility.

In an exemplary embodiment of the invention, a system is designed to be able to diagnose and quantify the risk of falls but also to provide treatment that is personalized to the person's needs using the VR system. The system uses a multi-modal treadmill training program augmented by VR that addresses both motor and cognitive aspects of fall risk and promotes motor learning critical for tasks that are key to safe ambulation. A pilot study was conducted in which five elderly women (67.1±6.5 years) with a history of falls trained for 18 sessions (3 per week×6 weeks), using the system described here. This training regimen was chosen as it was based on motor learning principles to maximize performance, motor learning and plasticity. Training was set at 3 times a week to allow for intensive treatment and consolidation of implicit information. Each session lasted approximately 1 hour including rest breaks, with actual walking time of approximately 50 minutes (beginning with 20 minutes in the first session and adding 2 minutes to each session). Training duration was set at 6 weeks to provide an opportunity for learning to take place and maximize retention. Other parameters may be used as well, for example, longer or shorter sessions, longer or shorter durations and/or changes in training intensity over time. Training progression was individualized to meet the needs of the participant. The virtual environment (VE) consisted of, for example, one or more obstacles, different pathways, narrow corridors and/or distracters, which may require modulations of step amplitude in one, two or three planes (e.g., height and width) coordinated with walking behavior. The speed, orientation, size, frequency of appearance and/or shape of the targets may be manipulated according to individual needs following a standardized protocol. Environmental features (e.g., visibility, settings and/or distractions) may be adjusted to increase training complexity. The VE imposed a cognitive load requiring attention and response selection and/or processing of rich visual stimuli involving several perceptual processes. In the experiment, the system provided visual and auditory feedback of successful or unsuccessful task performance to enhance motor learning. In an exemplary embodiment of the invention, the system is adaptable in that training parameters were adjusted to the clinical needs of the individual participant. Each training session lasted about 45 minutes and started with 5 minutes of "warm up" (only walking on the treadmill). After each warm-up phase, the VR simulation was introduced. The duration of continuous walking before rest breaks (typically three to five minutes initially) and the total walking time were also increased throughout the sessions. Feedback was given to the participant in the form of knowledge of results as a measure of scoring on the obstacle avoidance tasks and knowledge of performance in the form of auditory and visual feedback if the subject contacted a (virtual) obstacle. The feedback was intended to enhance motor learning and enable the modification of locomotion strategies to be able to avert falls.

After training, gait speed over-ground significantly improved during usual walking. More importantly, gait speed and stride time as well as variability improved during walking under dual tasking and while negotiating over-ground obstacles. Dual task cost and over-ground obstacle clearance also improved. The subjects were followed for 6 months post intervention and the frequency of falls was recorded during this period using fall calendars. In the follow up assessment, subjects reported that their function at home improved as well as their confidence in walking. In addition there was a decrease of 73% in the frequency of falls in the 6 months post-training as compared to 6 months pre-training suggesting that the VR intervention may be effective for older adults with a history of falls, may improve physical performance, improve gait during complex challenging conditions, decrease the risk of falls and may reduce falls.

General

It is expected that during the life of a patent maturing from this application many relevant display technologies will be developed and the scopes of the terms display and virtual reality are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of assessment of impairment, comprising:
presenting a subject with a plurality of motor and cognitive dual tasking provocations delivered by virtual reality (VR) on a display during locomotion selected to provoke at least one gait pathology associated with dual tasking, at least one of said provocations including a vertical component, wherein at least a partial virtual representation of movement of the feet of said subject viewed from the back is presented on said display at a distance from the eyes of said subject as part of a task designed to allow negotiation of said provocations by said partial virtual representation of the feet movement of said subject viewed from the back on said display, wherein said at least a partial virtual representation indicating movement of the feet of the subject gives the subject feedback as to negotiating vertical and horizontal obstacles, wherein said feedback includes presenting by said VR a vertical distance of a forefoot of the subject from the obstacle, wherein said presenting in said VR includes presenting an avatar in said VR, said avatar including at least the foot of the subject passing over the obstacle while the subject is walking; and wherein said display is fixed relative to a surface on which said subject walks;
measuring one or more physiological parameters of the subject during said locomotion; and
assessing a plurality of impairments based on said measuring, each of said impairments comprise one or more of cognitive and motor dual tasking associated impairments, wherein said cognitive impairments comprise one or more of executive function, attention, planning, and visual spatial processing.

2. A method according to claim 1, further comprising generating a training program based on said assessing wherein said training program comprises provocations.

3. A method according to claim 2, wherein said training program comprises reaction to obstacles presented on said display.

4. A method according to claim 3, wherein said obstacles comprise at least one vertical obstacle or at least one horizontal obstacle.

5. A method according to claim 1, wherein presenting comprises presenting situations of varying complexity.

6. A method according to claim 1, wherein presenting comprises presenting provocations both expected to induce falls or near falls and those expected not to induce falls or near falls.

7. A method according to claim 1, wherein presenting comprises presenting dual motor and cognitive tasks.

8. A method according to claim 1, wherein presenting comprises personalizing the presentation to a subject performance and/or a subject clinical history.

9. A method according to claim 1, comprising identifying one or more parameters of a situation and/or a trigger which induce falls or near falls in the subject.

10. A method according to claim 9, comprising setting up a training program responsive to the identifying.

11. A method according to claim 1, comprising detecting a near fall based on a change in a pattern of data from one or more movement sensors, with the support of one or more additional physiological sensors.

12. A method according to claim 1, comprising detecting a fall or near fall in a person having fewer than 1 fall or near fall in 10,000 steps in daily life.

13. A method according to claim 1, comprising increasing a rate of falls or near falls over average daily activities by a factor of at least 10.

14. A method according to claim 1, wherein said assessing is based on change of activity in frontal lobes of the subject.

15. A method according to claim 14, wherein said change in activity is detected using EEG.

16. A method according to claim 14, wherein an increase in blood flow to a frontal lobe is taken to indicate a gait disorder due to lack of or over activity in the frontal lobes.

17. A method according to claim 14, wherein a decrease in blood flow to a frontal lobe is taken to indicate a gait disorder due to frontal lobe dysfunction.

18. A method according to claim 1, wherein said one or more physiological parameters includes an anticipatory postural adjustment.

19. A method according to claim 1, wherein said provocations comprise one or more obstacles.

20. A method according to claim 19, wherein said one or more obstacles comprise at least one vertical obstacle or at least one horizontal obstacle.

21. A method according to claim 19, wherein said negotiation of said obstacles comprises stepping over said one or more obstacles presented on said display, by said partial virtual representation of the feet movement of said subject viewed from the back on said display.

22. A method according to claim 19, wherein said one or more obstacles comprise obstacles with varying height.

23. A method according to claim 1, wherein said presenting comprises presenting said plurality of provocations to said at least partial virtual representation of said subject on said display.

24. A method according to claim 1, comprising:
selecting by a controller said plurality of motor and cognitive dual tasking provocations personalized for a particular subject, wherein said plurality of motor and cognitive dual tasking provocations are selected to provoke at least one gait pathology in said particular subject.

25. A method according to claim 1, wherein said assessing comprises assessing cognitive and/or motor success in response to said motor and cognitive dual tasking provocations based on said measured physiological parameters.

26. A method according to claim 1, wherein said virtual representation of movement of the feet viewed from the back comprises an indication of a shoe.

27. A method according to claim 1, wherein said measuring the subject's activity in response to the provocations includes measuring at least one of clearance of an obstacle during obstacle negotiation, changes in strides between obstacles, and reaction time in regards to the provocations.

28. The method according to claim 27, wherein said changes in stride between obstacles includes changes in at least one of step length, foot clearance, gait asymmetry, gait variability, and base of support.

29. The method according to claim 1, further including measuring changes in performance across a plurality of sessions.

30. The method according to claim 1, wherein said presenting a plurality of provocations includes selecting a plurality of provocations personalized for the subject to improve performance of the subject.

31. The method according to claim 1, further including measuring the subject's activity in response to said provocations during said locomotion, wherein said measuring of the subject's activity is performed by at least one camera, and wherein assessing includes assessing a plurality of impairments based on said measuring said physiological parameters and based on said measuring the subject's activity in response to the provocations.

32. The method according to claim 31, wherein at least one camera readable marker is attached to the subject, and wherein said measuring the subject's activity is performed by said at least one camera by reading the at least one readable marker.

33. The method according to claim 1, further including measuring clearance over a virtual obstacle.

34. The method according to claim 1, wherein said feedback indicates clearance of the obstacle by at least the foot in both a vertical direction and a horizontal direction.

35. The method according to claim 1, said method for providing treatment of the subject's impairment, said treatment being personalized to the subject's needs using the VR system.

36. Apparatus for gait based assessment of a subject, comprising:
(a) a display;
(b) a controller configured to:
present at least a partial virtual representation of movement of the feet of said subject viewed from the back, at a distance from the eyes of said subject on the display and present a plurality of motor and cognitive dual tasking provocations during locomotion calculated to induce a fall or near fall on the display, at least one of said provocations including a vertical component, wherein said dual tasking provocations comprise one or more obstacles presented on said display, and wherein said at least a partial virtual representation indicates movement of the feet of the subject gives the subject feedback as to negotiating vertical and horizontal obstacles, wherein said feedback includes presenting by said VR a vertical distance of a forefoot of the subject from the obstacle, wherein said presenting in said VR includes presenting an avatar in said VR, said avatar including at least the foot of the subject passing over the obstacle while the subject is walking;
measure one or more physiological parameters of the subject during said locomotion;
assess a plurality of impairments based on one or more measured physiological parameters, each of said impairments comprise cognitive and motor dual tasking associated conditions, and wherein said cognitive conditions comprise one or more of executive function, attention, planning and visual spatial processing.

37. Apparatus according to claim 36, wherein said controller is configured to select said one or more provocations personalized for a particular subject.

38. Apparatus according to claim 37, wherein said controller is configured to select said one or more provocations in response to measurement by a system of subject activity.

39. Apparatus according to claim 37, wherein said controller is configured to modify a parameter of a selected provocation in response to measurement by a system of subject activity.

40. Apparatus according to claim 36, wherein said display is a virtual reality (VR) display.

41. Apparatus according to claim 36, comprising a plurality of wearable modules.

42. Apparatus according to claim 41, wherein a module is wireless and includes one or both of a sensor and an actuator.

43. Apparatus according to claim 36, comprising a treadmill controlled by said controller.

44. Apparatus according to claim 36, wherein said controller is configured to detect a fall and a near fall.

45. Apparatus according to claim 44, wherein said detection is based, at least in part, on one or both of a heart rate and an indication of frontal lobe activity.

46. Apparatus according to claim 36, wherein said controller is configured to measure at least an indication of brain activity.

47. Apparatus according to claim 36, wherein said controller is configured to generate a virtual reality simulation on said screen comprising negotiation of said one or more obstacles.

48. Apparatus according to claim 47, wherein said one or more obstacles comprise at least one vertical obstacle or at least one horizontal obstacle.

49. Apparatus according to claim 36, wherein said controller presents said one or more provocations to said at least a partial representation of said subject on said display.

50. Apparatus according to claim 36, wherein said controller is configured to assess cognitive and/or motor success in response to said provocations based on said measured physiological parameters.

51. Apparatus according to claim 36, wherein said virtual representation of movement of the feet viewed from the back comprises an indication of a shoe.

52. A method of assessment of impairment, comprising:
presenting a subject with a plurality of motor and cognitive dual tasking provocations delivered by virtual reality (VR) environment during locomotion selected to provoke at least one gait pathology associated with dual tasking, at least one of said provocations including a vertical component, wherein at least a partial virtual representation of movement of the feet of said subject viewed from the back is presented in said VR environment as part of a task designed to allow negotiation of said provocations by said partial virtual representation of the feet movement of said subject viewed from the back, wherein said at least a partial virtual representation indicating movement of the feet of the subject gives the subject feedback as to negotiating vertical and horizontal obstacles, wherein said feedback includes presenting in said VR environment a vertical distance of a forefoot of the subject from the obstacle, wherein said presenting in said VR environment includes presenting an avatar in said VR environment, said avatar including at least the foot of the subject passing over the obstacle while the subject is walking;
measuring one or more physiological parameters of the subject during said locomotion; and
assessing a plurality of impairments based on said measuring, each of said impairments comprise one or more of cognitive and motor dual tasking associated impairments, wherein said cognitive impairments comprise one or more of executive function, attention, planning, and visual spatial processing.

* * * * *